(12) United States Patent
Penn et al.

(10) Patent No.: US 8,445,453 B2
(45) Date of Patent: May 21, 2013

(54) CCR LIGANDS FOR STEM CELL HOMING

(75) Inventors: Marc S. Penn, Beachwood, OH (US); Matthew Kiedrowski, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 11/157,603

(22) Filed: Jun. 21, 2005

(65) Prior Publication Data

US 2006/0182712 A1    Aug. 17, 2006

Related U.S. Application Data

(60) Provisional application No. 60/581,571, filed on Jun. 21, 2004.

(51) Int. Cl.
*A61K 48/00* (2006.01)
*A01N 63/00* (2006.01)

(52) U.S. Cl.
USPC ........................................ 514/44 R; 424/93.1

(58) Field of Classification Search
USPC ........................................ 514/44 R; 424/93.1
See application file for complete search history.

(56) References Cited

U.S. PATENT DOCUMENTS

| | | | | |
|---|---|---|---|---|
| 6,100,389 A * | 8/2000 | Li et al. | ........................ | 536/23.5 |
| 6,387,369 B1 * | 5/2002 | Pittenger et al. | ............. | 424/93.7 |
| 2002/0061587 A1 * | 5/2002 | Anversa | ........................ | 435/366 |
| 2003/0125615 A1 | 7/2003 | Schwartz | | |
| 2004/0037811 A1 | 2/2004 | Penn et al. | | |
| 2004/0213770 A1 * | 10/2004 | Seward et al. | ............. | 424/93.71 |
| 2004/0258669 A1 * | 12/2004 | Dzau et al. | ................. | 424/93.21 |
| 2007/0020230 A1 * | 1/2007 | Kaps et al. | .................... | 424/85.1 |

FOREIGN PATENT DOCUMENTS

| | | |
|---|---|---|
| EP | 1 415 661 A1 | 5/2004 |
| JP | 2004-149532 | 5/2004 |
| WO | WO 03/090512 | 11/2003 |
| WO | WO 2004/084931 A1 | 10/2004 |

OTHER PUBLICATIONS

Miller and Vile, Targeted vectors for gene therapy, FASEB J. 9(2): 190-9, 1995.*
Deonarain, Ligand-targeted receptor-mediated vectors for gene delivery, Exp. Opin. Ther. Patents 8(1): 53-69, 1998; Ashley Publications Ltd. ISSN 1354-3776.*
Verma and Somia, Gene therapy—promises, problems and prospects, Nature 389: 239-42, 1997.*
Crystal, Transfer of genes to humans: early lessons and obstacles to success, Science 270: 404-10, 1995.*
Pouton and Seymour, Key issues in non-viral gene delivery, Adv Drug Deliv Rev. 46(1-3): 187-203, 2001.*
Read et al., Barriers to gene delivery using synthetic vectors, Adv Genet. 53: 19-46, 2005.*
Dobson, Gene therapy progress and prospects: magnetic nanoparticle-based gene delivery. Gene Ther. 13(4): 283-7, 2006.*
Schenk et al., Monocyte chemotactic protein-3 is a myocardial mesenchymal stem cell homing factor. Stem Cells, 25(1): 245-51, 2007.*
Penn et al., Role of stem cell homing in myocardial regeneration. Int J Cardiol. 95 Suppl 1:S23-5, 2004.*
Wetzel et al., Transduction of human MCP-3 by a parvoviral vector induces leukocyte infiltration and reduces growth of human cervical carcinoma cell xenografts. J Gene Med. 3(4):326-37, 2001.*
Terreence et al., Enhanced myocardial angiogenesis by gene transfer with transplanted cells, Circulation, 104 (supplement 1): I-218-I-222, 2001.*
Schwarze et al., In vivo protein transduction: delivery of a biologically active protein into the mouse. Science 285(5433): 1569-72, 1999.*
Gloor et al., Molecular and cellular permeability control at the blood-brain barrier. Brain Res Brain Res Rev. 36(2-3): 258-64, 2001.*
Panchision, The role of oxygen in regulating neural stem cells in development and disease, J Cell Physiol. 220(3):562-8, 2009.*
Penn et al., Autologous cell transplantation for the treatment of damaged myocardium, Prog Cardiovasc Dis. 45(1):21-32, 2002.*
Post et al. Molecular characterization of two murine eosinophil beta chemokine receptors, J Immunol. 155(11):5299-305, 1995.*
Fioretti et al., Reduced tumorigenicity and augmented leukocyte infiltration after monocyte chemotactic protein-3 (MCP-3) gene transfer: perivascular accumulation of dendritic cells in peritumoral tissue and neutrophil recruitment within the tumor, J Immunol. 161(1):342-6, 1998.*
Omura, T. et al., Involvement of Apoptosis Signal-Regulating Kinase-1 on Angiotensin II-Induced Monocyte Chemoattractant Protein-1 Expression, *Aterioscier Thromb Vasc Biol.* 2004;24:270-275.
Wang, Lei et al., MCP-1, MIP-1, IL-8 and Ischemic Cerebral Tissue Enhance Human Bone Marrow Stromal Cell Migration in Interface Culture, *Hermatology*, 2002;7(2):113-117.
Ji, Jun Feng et al., Interactions of Chemokines and Chemokine Receptors Mediate the Migration of Mesenchymal Stem Cells to the Impaired Site in the Brain After Hypoglossal Nerve Injury, *Stem Cells*, 2004;22:415-427.
Askari, Arman T. et al., Effect of Stromal-Cell-Derived Factor 1 on Stem-Cell Homing and Tissue Regeneration in Ischaemic Cardiomyopathy, *The Lancet*, 2003;362:697-703.

* cited by examiner

*Primary Examiner* — Thaian N Ton
(74) *Attorney, Agent, or Firm* — Woodcock Washburn LLP

(57) ABSTRACT

Chemokines ligands to at least one of CCR1, CCR2, CCR3, or CCR5 can be used to home stem cells for therapeutic applications.

17 Claims, 5 Drawing Sheets

CCR LIGANDS FOR STEM CELL HOMING

RELATED APPLICATION

This application claims the benefit of U.S. Provisional Application No. 60/581,571, which was filed on Jun. 21, 2004 and is incorporated herein by reference.

FIELD OF THE INVENTION

The present invention relates to chemokines and particularly to use of chemokines that induce chemotaxis of stem cells.

BACKGROUND OF THE INVENTION

Acute myocardial infarction (MI) remains the leading cause of morbidity and mortality in western society. Despite recent therapeutic advances predominantly targeted at restoring antegrade perfusion in the infarct-related artery, a "ceiling" of benefit appears to exist. Topol, E. J. *Lancet* 357, 1905-1914 (2001). A substantial proportion of patients who experience an acute myocardial infarction (MI) ultimately develop congestive heart failure (CHF) largely as a result of left ventricular (LV) remodeling, a process involving myocardial thinning, dilation, decreased function, ultimately leading to death. Robbins, M. A. & O'Connell, J. B., pp. 3-13 (Lippincott-Raven, Philadelphia, 1998). Pfeffer, J. M., Pfeffer, M. A., Fletcher, P. J. & Braunwald, E. *Am. J. Physiol* 260, H1406-H1414 (1991). Pfeffer, M. A. & Braunwald, E. *Circulation* 81, 1161-1172 (1990).

One method to treat this process following myocardial infarction involves cell therapy. Penn, M. S. et al. *Prog. Cardiovasc. Dis.* 45, 21-32 (2002). Transplantation has focused on using a variety of cell types including differentiated cells, such as skeletal myoblasts, cardiac myocytes, smooth muscle cells, and fibroblasts, or bone marrow derived cells. Koh, G. Y., Klug, M. G., Soonpaa, M. H. & Field, L. J. *J. Clin. Invest* 92, 1548-1554 (1993). Taylor, D. A. et al. *Nat. Med.* 4, 929-933 (1998). Jain, M. et al. *Circulation* 103, 1920-1927 (2001). Li, R. K. et al. *Ann. Thorac. Surg.* 62, 654-660 (1996). Etzion, S. et al. *J. Mol. Cell Cardiol.* 33, 1321-1330 (2001). Li, R. K., Jia, Z. Q., Weisel, R. D., Merante, F. & Mickle, D. A. *J. Mol. Cell Cardiol.* 31, 513-522 (1999). Yoo, K. J. et al. *Yonsei Med. J* 43, 296-303 (2002). Sakai, T. et al. *Ann. Thorac. Surg.* 68, 2074-2080 (1999). Sakai, T. et al. *J. Thorac. Cardiovasc. Surg.* 118, 715-724 (1999). Orlic, D. et al. *Nature* 410, 701-705 (2001). Tomita, S. et al. *J. Thorac. Cardiovasc. Surg.* 123, 1132-1140 (2002).

A growing body of literature suggests that stem cell mobilization to the heart and differentiation into cardiac myocytes is a naturally occurring process. Jackson, K. A. et al. *J. Clin. Invest* 107, 1395-1402 (2001). Quaini, F. et al. *N. Engl. J. Med.* 346, 5-15 (2002). This process occurs at a rate insufficient to result in meaningful recovery of left ventricular function following myocardial infarction. Id. Recently, studies have demonstrated the possibility of regenerating damaged myocardium either through the direct injection of stem cells into the blood stream, or via chemical mobilization of stem cells from the bone marrow prior to the myocardial infarction. These studies have demonstrated the ability of stem cells to home to the infarct zone in the peri-infarct period, as well as for these cells to then differentiate into cardiac myocytes. Kocher, A. A. et al. *Nat. Med.* 7, 430-436 (2001). Orlic, D. et al. *Proc. Natl. Acad. Sci. U.S.A.* 98, 10344-10349 (2001). Peled, A. et al. *Blood* 95, 3289-3296 (2000). Yong, K. et al. *Br. J. Haematol.* 107, 441-449 (1999). To date, all the studies have focused on the ability of stem cells to regenerate myocardium within 48 hours after myocardial infarction.

SUMMARY OF THE INVENTION

The present invention relates to chemokines that function as chemoattractants for stem cells that express or that are induced to express at least one of CCR1, CCR2, CCR3, or CCR5, such as mesenchymal stems cells (MSCs), multipotent adult progenitor cells (MAPCs), and/or other stem cells. The chemokines in accordance with the present invention can be provided in a tissue of a mammalian subject to induce mobilization of stem cells to the tissue for therapeutic applications and/or cellular therapy. The stem cells, which are induced, can differentiate into specialized and/or partially specialized cells that can repopulate (i.e., engraft) and partially or wholly restore the normal function of the tissue being treated. One example of a particular type of stem cell that can be induced by the chemokines in accordance with the present invention is a mesenchymal stem cell (MSC). Another example of a stem cell that can be potentially induced by chemokines in accordance with the presence is a multipotent adult progenitor cell (MAPC). Still other examples of stem cells are those that are genetically modified to express at least one of CCR1, CCR2, CCR3, or CCR5.

In accordance with an aspect of invention, the chemokine comprises a ligand to at least one of CCR1, CCR2, CCR3, or CCR5. Chemokine ligands to at least one of CCR1, CCR2, CCR3, or CCR5 were found to be chemoattractants for MSCs, MAPCs, and/or other stem cells in a mammalian subject. Chemokine ligands to at least one of CCR1, CCR2, CCR3, or CCR5 can include monocyte chemotactic proteins 1-5, (i.e., MCP-1, MCP-2, MCP-3, MCP-4, and MCP-5), macrophage inflammatory proteins 1-2, (i.e., MIP-1α, MIP-1β, and MIP-2), and any other ligand (e.g., protein, polypeptide, etc.) that is capable of binding to at least one of CCR1, CCR2, CCR3, or CCR5 and that functions as a chemoattractant of MSCs, MAPCs, and/or other stem cells.

The MCP-1, MCP-2, MCP-3, MCP-4, MCP-5, MIP-1α, MIP-1β, and/or MIP-2 in accordance with the present invention can have amino sequences substantially similar to native mammalian MCP-1, MCP-2, MCP-3, MCP-4, MCP-5, MIP-1α, MIP-1β, and/or MIP-2 as well as be a variant of native mammalian MCP-1, MCP-2, MCP-3, MCP-4, MCP-5, MIP-1α, MIP-1β, and/or MIP-2, such as a fragment, analog and derivative of mammalian MCP-1, MCP-2, MCP-3, MCP-4, MCP-5, MIP-1α, MIP-1β, and/or MIP-2.

In accordance with another aspect of the invention, the chemokine ligands to at least one of CCR1, CCR2, CCR3, or CCR5 can be provided in the tissue by introducing an expression vector into the tissue. The expression vector includes a nucleic acid encoding for the chemokine ligand to at least one of CCR1, CCR2, CCR3, or CCR5. Optionally, the expression vector can include a tissue specific promoter, such as a tissue specific promoter directed to myocardial tissue.

In accordance with yet another aspect of the present invention, the chemokine ligand to at least one of CCR1, CCR2, CCR3, or CCR5 can be provided in the tissue by introducing cells into the tissue that have been cultured ex vivo. The cells that have been cultured ex vivo can comprise allogenic and/or autologous cells, which have been harvested from the subject to be treated. The cells that are introduced into the tissue to be treated can be transfected with an expression vector prior to being introduced into the infarcted tissue. The expression vector can include a nucleic acid encoding the chemokine ligand to at least one of CCR1, CCR2, CCR3, or CCR5.

The present invention also relates to a method of treating infarcted tissue of a mamalian subject. In the method, chemokine ligands to at least one of CCR1, CCR2, CCR3, or CCR5 can be provided in the infarcted tissue and/or areas proximate the infarcted tissue. The concentration (or number) of stem cells that express or that are induced to express at least one of CCR1, CCR2, CCR3, or CCR5 in the peripheral blood of the infarcted tissue can be increased from the first concentration to a second concentration while the chemokine ligands to at least one of CCR1, CCR2, CCR3, or CCR5 are provided in the infarcted tissue.

The number of stem cells that express or that are induced to express at least one of CCR1, CCR2, CCR3, or CCR5 in the peripheral blood can be increased by injecting stem cells into the peripheral blood and/or arterial or venous infusion of the stem cells into the mammalian subject being treated. One example of a particular type of stem cell that can be injected or infused in accordance with the present invention is a mesenchymal stem cell (MSC). Another example of a stem cell that can be potentially injected or infused is a multipotent adult progenitor cell (MAPC). Still other examples of stem cells are those that are genetically modified to express at least one of CCR1, CCR2, CCR3, or CCR5.

BRIEF DESCRIPTION OF THE DRAWINGS

Further features of the present invention will become apparent to those skilled in the art to which the present invention relates from reading the following description of the invention with reference to the accompanying drawings in which.

DESCRIPTION OF THE EMBODIMENTS

Figure 1:
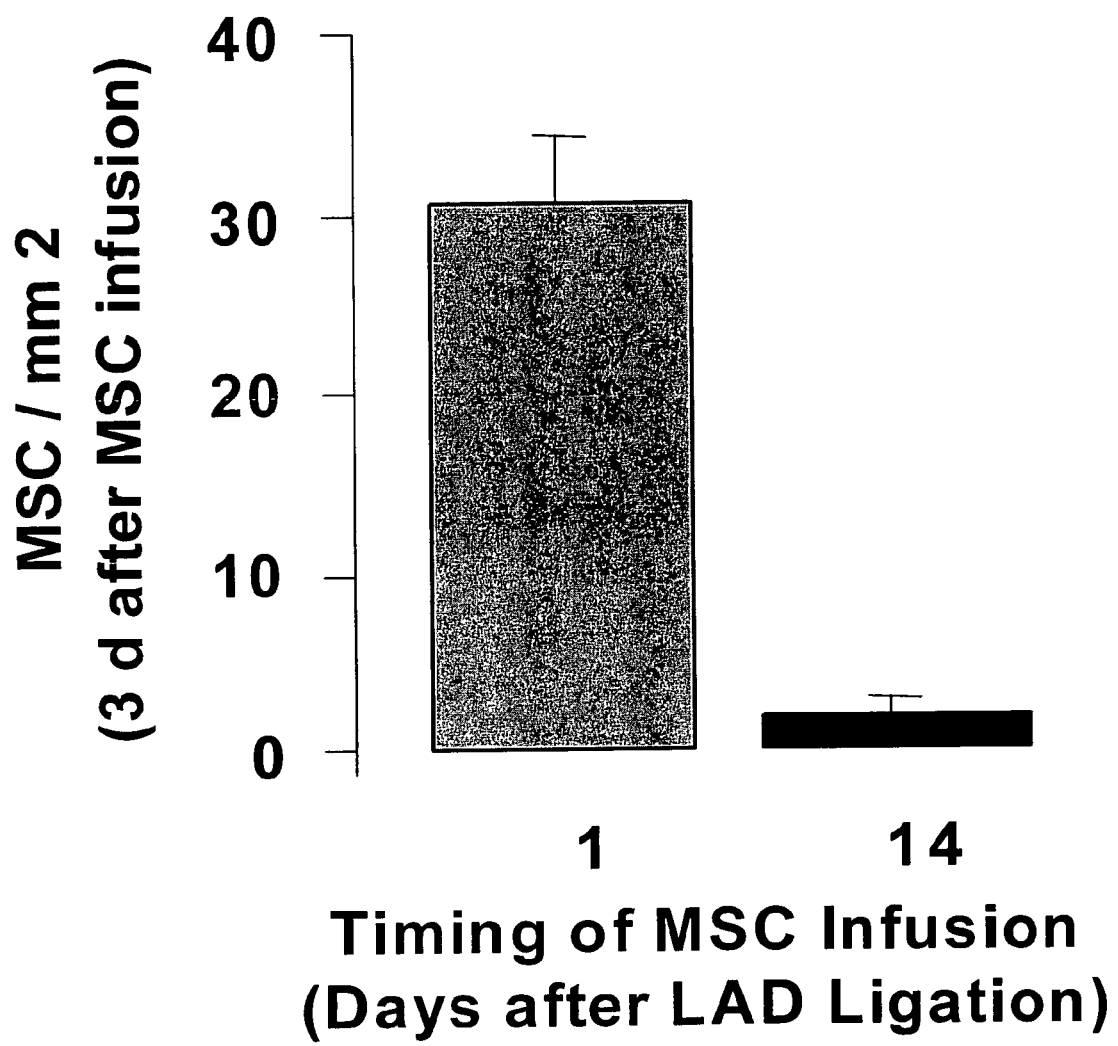
FIG. 1 is a graph comparing the number of MSCs per unit area in the infarct zone of rats infused with MSCs, respectively, three days after LAD ligation and 14 days after LAD ligation.

Unless otherwise defined, all technical terms used herein have the same meaning as commonly understood by one of ordinary skill in the art to which this invention belongs. Commonly understood definitions of molecular biology terms can be found in, for example, Rieger et al., Glossary of Genetics: Classical and Molecular, 5th edition, Springer-Verlag: New York, 1991; and Lewin, Genes V, Oxford University Press: New York, 1994.

Methods involving conventional molecular biology techniques are described herein. Such techniques are generally known in the art and are described in detail in methodology treatises, such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

The present invention relates to chemokines that function as chemoattractants for stem cells that express or are induced to express at least one of CCR1, CCR2, CCR3, or CCR5, such as mesenchymal stems cells (MSCs), multipotent adult progenitor cells (MAPCs), and/or other stem cells. The chemokines in accordance with the present invention can be provided in a tissue of a mammalian subject to induce mobilization of stem cells to the tissue for therapeutic applications and/or cellular therapy. The stem cells, which are induced, can differentiate into specialized and/or partially specialized cells that can repopulate (i.e., engraft) and partially or wholly restore the normal function of the tissue being treated.

Mammalian subjects in accordance with the invention can include any mammal, such as human beings, rats, mice, cats, dogs, goats, sheep, horses, monkeys, apes, rabbits, cattle, etc. The mammalian subject can be in any stage of development including adults, young animals, and neonates. Mammalian subjects can also include those in a fetal stage of development.

Stem cells that express or are induced to express at least one of CCR1, CCR2, CCR3, or CCR5 in accordance with the present invention include unspecialized cells that can self-renew indefinitely and that can differentiate into more mature cells with specialized functions. In humans, stem cells have been identified in the inner cell mass of the early embryo, in some tissues of the fetus, the umbilical cord and placenta, and in several adult organs. In some adult organs, stem cells can give rise to more than one specialized cell type within that organ. Stem cells, which are able to differentiate into cell types beyond those of which they normally reside exhibit plasticity. When a stem cell is found to give rise to multiple tissue types associated with different organs it is referred to as multipotent or pluripotent.

One example of a particular type of stem cell that can be induced by the chemokines in accordance with the present invention is a mesenchymal stem cell (MSC). MSCs include the formative pluripotent blast or embryonic cells that differentiate into the specific types of connective tissues, (i.e., the tissue of the body that support specialized elements, particularly including adipose, osseous, cartilaginous, elastic, muscular, and fibrous connective tissues depending on various in vivo or in vitro environmental influences. These cells can be present in bone marrow, blood, dermis, and periosteum and can be isolated and purified using various well known methods, such as those methods disclosed in U.S. Pat. No. 5,197,985 to Caplan and Haynesworth, herein incorporated by reference, as well as other numerous literature references.

Another example of a stem cell that can be potentially induced by chemokines in accordance with the presence is a multipotent adult progenitor cell (MAPC). MAPCs in accordance with the present invention comprise adult progenitor or stem cells that are capable of differentiating into cells types beyond those of the tissues in which they normally reside (i.e., exhibit plasticity). Examples of MAPCs can include adult MSCs and hematopoietic progenitor cells. Sources of MAPCs can include bone marrow, blood, ocular tissue, dermis, liver, and skeletal muscle. By way of example, MAPCs comprising hematopoietic progenitor cells can be isolated and purified using the methods disclosed in U.S. Pat. No. 5,061,620, herein incorporated by reference, as well as other numerous literature sources.

Stems cells, such as MSCs, MAPCs, and/or other stem cells, can naturally express or be induced to express various CXC and CC chemokine receptors, including CXCR5, CCR-1, Cmkbr1L2, CCR2, CCR3, CCR5, CCR7, CCR8, CCR9, CMKOR1, and CX3CR1. It was found that chemokine ligands to at least one of CCR1, CCR2, CCR3, or CCR5 can function as chemoattractants for MSCs and/or MAPCs in a mammalian subject. The chemokine ligands to at least one of CCR1, CCR2, CCR3, or CCR5 can include monocyte chemotactic proteins 1-5, (i.e., MCP-1, MCP-2, MCP-3, MCP-4, and MCP-5), macrophage inflammatory proteins 1-2, (i.e., MIP-1α, MIP-1β, and MIP-2), and any other ligand (e.g., protein, polypeptide, etc.) that is capable of binding to at least of CCR1, CCR2, CCR3, or CCR5 and that functions as a chemoattractant of MSCs and/or MAPCs.

The MCP-1, MCP-2, MCP-3, MCP-4, MCP-5, MIP-1α, MIP-1β, and/or MIP-2 in accordance with the present invention can have amino sequences substantially similar to native mammalian MCP-1, MCP-2, MCP-3, MCP-4, MCP-5, MIP-1α, MIP-1β, and/or MIP-2. For example, the MCP-1, MCP-2, MCP-3, MCP-4, MCP-5, MIP-1α, MIP-1β, and/or MIP-2 can have amino sequences substantially similar to, respectively, SEQ ID NO: 1, SEQ ID NO: 2, SEQ ID NO: 3, SEQ ID NO: 4, SEQ ID NO: 5, SEQ ID NO:6, SEQ ID NO:7, and SEQ ID NO: 8. SEQ ID NO: 1, SEQ ID NO: 2, SEQ ID NO: 3, SEQ ID NO:4, SEQ ID NO: 5, SEQ ID NO: 6, SEQ ID NO: 7, and SEQ ID NO: 8 comprise, respectively, the amino acid sequences for human MCP-1, MCP-2, MCP-3, MCP-4, MCP-5, mouse MIP-1α, rat MIP-1β, and mouse MIP-2 and are substantially similar to the nucleic sequences of, respectively, GenBank Accession Nos. AAM54046, CAA76341, CAA50407, CAA04888, AAS28707, NP035467, NP446310, and NP063316.

The MCP-1, MCP-2, MCP-3, MCP-4, MCP-5, MIP-1α, MIP-1β, and/or MIP-2 of the present invention can also be a variant of native mammalian MCP-1, MCP-2, MCP-3, MCP-4, MCP-5, MIP-1α, MIP-1β, and/or MIP-2, such as a fragment, analog and derivative of mammalian MCP-1, MCP-2, MCP-3, MCP-4, MCP-5, MIP-1α, MIP-1β, and/or MIP-2. Such variants can include, for example, a polypeptide encoded by a naturally occurring allelic variant of a native MCP-1, MCP-2, MCP-3, MCP-4, MCP-5, MIP-1α, MIP-1β, and/or MIP-2 gene (i.e., a naturally occurring nucleic acid that encodes a naturally occurring mammalian MCP-1, MCP-2, MCP-3, MCP-4, MCP-5, MIP-1α, MIP-1β, and/or MIP-2), a polypeptide encoded by an alternative splice form of a native MCP-1, MCP-2, MCP-3, MCP-4, MCP-5, MIP-1α, MIP-1β, and/or MIP-2 gene, a polypeptide encoded by a homolog or ortholog of a native MCP-1, MCP-2, MCP-3, MCP-4, MCP-5, MIP-1α, MIP-1βP, and/or MIP-2 gene, and a polypeptide encoded by a non-naturally occurring variant of a native MCP-1, MCP-2, MCP-3, MCP-4, MCP-5, MIP-1α, MIP-1β, and/or MIP-2 gene.

MCP-1, MCP-2, MCP-3, MCP-4, MCP-5, MIP-1α, MIP-1β, and/or MIP-2 variants have a peptide (or amino acid) sequence that differs from native MCP-1, MCP-2, MCP-3, MCP-4, MCP-5, MIP-1α, MIP-1β, and/or MIP-2 in one or more amino acids. The peptide sequence of such variants can feature a deletion, addition, or substitution of one or more amino acids of MCP-1, MCP-2, MCP-3, MCP-4, MCP-5, MIP-1α, MIP-1β, and/or MIP-2 protein. Amino acid insertions are preferably of about 1 to 4 contiguous amino acids, and deletions are preferably of about 1 to 10 contiguous amino acids. Variant MCP-1, MCP-2, MCP-3, MCP-4, MCP-5, MIP-1α, MIP-1β, and/or MIP-2 proteins substantially maintain a native MCP-1, MCP-2, MCP-3, MCP-4, MCP-5, MIP-1α, MIP-1β, and/or MIP-2 protein functional activity. Preferred MCP-1, MCP-2, MCP-3, MCP-4, MCP-5, MIP-1α, MIP-1β, and/or MIP-2 protein variants can be made by expressing nucleic acid molecules within the invention that feature silent or conservative changes.

MCP-1, MCP-2, MCP-3, MCP-4, MCP-5, MIP-1α, MIP-1β, and/or MIP-2 protein fragments corresponding to one or more particular motifs and/or domains or to arbitrary sizes, are within the scope of the present invention. Isolated peptidyl portions of MCP-1, MCP-2, MCP-3, MCP-4, MCP-5, MIP-1α, MIP-1β, and/or MIP-2 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a MCP-1, MCP-2, MCP-3, MCP-4, MCP-5, MIP-1α, MIP-1β, and/or MIP-2 protein of the present invention may be arbitrarily divided into fragments of desired length with no overlap of the fragments, or preferably divided into overlapping fragments of a desired length. The fragments can be produced recombinantly and tested to identify those peptidyl fragments which can function as agonists of a native MCP-1, MCP-2, MCP-3, MCP-4, MCP-5, MIP-1α, MIP-1β, and/or MIP-2 protein.

Variants of MCP-1, MCP-2, MCP-3, MCP-4, MCP-5, MIP-1α, MIP-1β, and/or MIP-2 protein can also include recombinant forms of the proteins. Recombinant polypeptides preferred by the present invention, in addition to a MCP-1, MCP-2, MCP-3, MCP-4, MCP-5, MIP-1α, MIP-1β, and/or MIP-2 protein, are encoded by a nucleic acid that can have at least 85% sequence identity with the nucleic acid sequence of a gene encoding a mammalian protein.

MCP-1, MCP-2, MCP-3, MCP-4, MCP-5, MIP-1α, MIP-1β, and/or MIP-2 protein variants can include agonistic forms of the protein that constitutively express the functional activities of a native MCP-1, MCP-2, MCP-3, MCP-4, MCP-5, MIP-1α, MIP-1β, and/or MIP-2 protein. Other protein variants can include those that are resistant to proteolytic cleavage, as for example, due to mutations, which alter protease target sequences. Whether a change in the amino acid sequence of a peptide results in a variant having one or more functional activities of a native MCP-1, MCP-2, MCP-3, MCP-4, MCP-5, MIP-1α, MIP-1β, and/or MIP-2 protein can be readily determined by testing the variant for a native MCP-1, MCP-2, MCP-3, MCP-4, MCP-5, MIP-1α, MIP-1β, and/or MIP-2 protein functional activity.

Nucleic acid molecules that encode the MCP-1, MCP-2, MCP-3, MCP-4, MCP-5, MIP-1α, MIP-1β, and/or MIP-2 protein can be a native or non-native nucleic acid and be in the form of RNA or in the form of DNA (e.g., cDNA, genomic DNA, and synthetic DNA). The DNA can be double-stranded or single-stranded, and if single-stranded may be the coding (sense) strand or non-coding (anti-sense) strand.

For example, nucleic acid molecules that encode the MCP-1, MCP-2, MCP-3, MCP-4, MCP-5, MIP-1α, MIP-1β, and/or MIP-2 can have sequences substantially similar to, respectively, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16 are substantially similar to the nucleic sequences of, respectively, GenBank Accession Nos. NM002982, NM005623, NM006273, NM005408, NM011331, NM013025, NM013652, and NM053647.

Other nucleic acid molecules that encode MCP-1, MCP-2, MCP-3, MCP-4, MCP-5, MIP-1α, MIP-1β, and/or MIP-2 protein within the invention can be variants of a native MCP-1, MCP-2, MCP-3, MCP-4, MCP-5, MIP-1α, MIP-1β, and/or MIP-2 protein gene, such as those that encode fragments, analogs and derivatives of a native MCP-1, MCP-2, MCP-3, MCP-4, MCP-5, MIP-1α, MIP-1β, and/or MIP-2 protein. Such variants may be, for example, a naturally occurring allelic variant of a native MCP-1, MCP-2, MCP-3, MCP-4, MCP-5, MIP-1α, MIP-1β, and/or MIP-2 gene, a homolog of a native MCP-1, MCP-2, MCP-3, MCP-4, MCP-5, MIP-1α, MIP-1β, and/or MIP-2 gene, or a non-naturally occurring variant of a native MCP-1, MCP-2, MCP-3, MCP-4, MCP-5, MIP-1α, MIP-1β, and/or MIP-2 gene. These variants have a nucleotide sequence that differs from a native MCP-1, MCP-2, MCP-3, MCP-4, MCP-5, MIP-1α, MIP-1β, and/or MIP-2 gene in one or more bases. For example, the nucleotide sequence of such variants can feature a deletion, addition, or substitution of one or more nucleotides of a native MCP-1, MCP-2, MCP-3, MCP-4, MCP-5, MIP-1α, MIP-1β, and/or MIP-2 gene. Nucleic acid insertions are preferably of about 1 to 10 contiguous nucleotides, and deletions are preferably of about 1 to 10 contiguous nucleotides.

In other applications, variant native MCP-1, MCP-2, MCP-3, MCP-4, MCP-5, MIP-1α, MIP-1β, and/or MIP-2 proteins displaying substantial changes in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histidine, for (or by) an electronegative residue, e.g., glutamine or aspartine; or (d) a residue having a bulky side chain, e.g., phenylalanine, for (or by) one not having a side chain, e.g., glycine.

Naturally occurring allelic variants of a native MCP-1, MCP-2, MCP-3, MCP-4, MCP-5, MIP-1α, MIP-1β, and/or MIP-2 gene within the invention are nucleic acids isolated from mammalian tissue that have at least 75% sequence identity with a native MCP-1, MCP-2, MCP-3, MCP-4, MCP-5, MIP-1α, MIP-1β, and/or MIP-2 gene, and encode polypeptides having structural similarity to a native MCP-1, MCP-2, MCP-3, MCP-4, MCP-5, MIP-1α, MIP-1β, and/or MIP-2 protein. Homologs or orthologs of a native MCP-1, MCP-2, MCP-3, MCP-4, MCP-5, MIP-1α, MIP-1β, and/or MIP-2 gene within the invention are nucleic acids isolated from other species that have at least 75% sequence identity with the native gene, and encode polypeptides having structural similarity to a native MCP-1, MCP-2, MCP-3, MCP-4, MCP-5, MIP-1α, MIP-1β, and/or MIP-2 protein. Public and/or proprietary nucleic acid databases can be searched to identify other nucleic acid molecules having a high percent (e.g., 70% or more) sequence identity to a native MCP-1, MCP-2, MCP-3, MCP-4, MCP-5, MIP-1α, MIP-1β, and/or MIP-2 gene.

Non-naturally occurring MCP-1, MCP-2, MCP-3, MCP-4, MCP-5, MIP-1α, MIP-1β, and/or MIP-2 gene variants are nucleic acids that do not occur in nature (e.g., are made by the hand of man), have at least 75% sequence identity with a native MCP-1, MCP-2, MCP-3, MCP-4, MCP-5, MIP-1α, MIP-1β, and/or MIP-2 gene, and encode polypeptides having structural similarity to a native MCP-1, MCP-2, MCP-3, MCP-4, MCP-5, MIP-1α, MIP-1β, and/or MIP-2 protein. Examples of non-naturally occurring MCP-1, MCP-2, MCP-3, MCP-4, MCP-5, MIP-1α, MIP-1β, and/or MIP-2 gene variants are those that encode a fragment of a native MCP-1, MCP-2, MCP-3, MCP-4, MCP-5, MIP-1α, MIP-1β, and/or MIP-2 protein, those that hybridize to a native MCP-1, MCP-2, MCP-3, MCP-4, MCP-5, MIP-1α, MIP-1β, and/or MIP-2 gene or a complement of to a native MCP-1, MCP-2, MCP-3, MCP-4, MCP-5, MIP-1α, MIP-1β, and/or MIP-2 gene under stringent conditions, those that share at least 65% sequence identity with a native MCP-1, MCP-2, MCP-3, MCP-4, MCP-5, MIP-1α, MIP-1β, and/or MIP-2 gene or a complement of a native MCP-1, MCP-2, MCP-3, MCP-4, MCP-5, MIP-1α, MIP-1β, and/or MIP-2 gene, and those that encode a MCP-1, MCP-2, MCP-3, MCP-4, MCP-5, MIP-1α, MIP-1β, and/or MIP-2 fusion protein.

Nucleic acids encoding fragments of a native MCP-1, MCP-2, MCP-3, MCP-4, MCP-5, MIP-1α, MIP-1β, and/or MIP-2 protein within the invention are those that encode, amino acid residues of a native MCP-1, MCP-2, MCP-3, MCP-4, MCP-5, MIP-1α, MIP-1β, and/or MIP-2 protein. Shorter oligonucleotides that encode or hybridize with nucleic acids that encode fragments of a native MCP-1, MCP-2, MCP-3, MCP-4, MCP-5, MIP-1α, MIP-1β, and/or MIP-2 protein can be used as probes, primers, or antisense molecules. Longer polynucleotides that encode or hybridize with nucleic acids that encode fragments of a native MCP-1, MCP-2, MCP-3, MCP-4, MCP-5, MIP-1α, MIP-1β, and/or MIP-2 protein can also be used in various aspects of the invention. Nucleic acids encoding fragments of a MCP-1, MCP-2, MCP-3, MCP-4, MCP-5, MIP-1α, MIP-1β, and/or MIP-2 can be made by enzymatic digestion (e.g., using a restriction enzyme) or chemical degradation of the full length native MCP-1, MCP-2, MCP-3, MCP-4, MCP-5, MIP-1α, MIP-1β, and/or MIP-2 gene or variants thereof.

Nucleic acids that hybridize under stringent conditions to one of the foregoing nucleic acids can also be used in the invention. For example, such nucleic acids can be those that hybridize to one of the foregoing nucleic acids under low stringency conditions, moderate stringency conditions, or high stringency conditions are within the invention.

Nucleic acid molecules encoding an MCP-1, MCP-2, MCP-3, MCP-4, MCP-5, MIP-1α, MIP-1β, and/or MIP-2 fusion protein may also be used in the invention. Such nucleic acids can be made by preparing a construct (e.g., an expression vector) that expresses an MCP-1, MCP-2, MCP-3, MCP-4, MCP-5, MIP-1α, MIP-1β, and/or MIP-2 fusion protein when introduced into a suitable target cell. For example, such a construct can be made by ligating a first polynucleotide encoding a MCP-1, MCP-2, MCP-3, MCP-4, MCP-5, MIP-1α, MIP-1β, and/or MIP-2 protein fused in frame with a second polynucleotide encoding another protein such that expression of the construct in a suitable expression system yields a fusion protein.

The oligonucleotides of the invention can be DNA or RNA or chimeric mixtures or derivatives or modified versions thereof, single-stranded or double-stranded. Such oligonucleotides can be modified at the base moiety, sugar moiety, or phosphate backbone, for example, to improve stability of the molecule, hybridization, etc. Oligonucleotides within the invention may additionally include other appended groups such as peptides (e.g., for targeting target cell receptors in vivo), or agents facilitating transport across the cell membrane, hybridization-triggered cleavage. To this end, the oligonucleotides may be conjugated to another molecule, e.g., a peptide, hybridization triggered cross-linking agent, transport agent, hybridization-triggered cleavage agent, etc.

The chemokine ligands to at least one of CCR1, CCR2, CCR3, or CCR5 (e.g., MCP-1, MCP-2, MCP-3, MCP-4, MCP-5, MIP-1α, MIP-1β, and/or MIP-2), can be provided in the tissue of the mammalian subject to be treated by administering the chemokine ligand to the tissue neat or in a pharmaceutical composition. The pharmaceutical composition comprising the chemokine ligand can be delivered by various methods depending on the tissue, which is to be treated. In one aspect, the pharmaceutical composition can be delivered by injection. The routes for administration can be subcutaneous or parenteral including, for example, intravenous, intraarterial, intramuscular, intraperitoneal, intramyocardial, and transendocardial.

When administering the chemokine ligand parenterally, it will generally be formulated in a unit dosage injectable form (e.g., solution, suspension, and/or emulsion). Examples of pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol, and the like), suitable mixtures thereof and vegetable oils.

Proper fluidity can be maintained, for example, by the use of a coating, such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various amounts of the other ingredients, as desired.

Alternatively, the chemokine ligands to at least one of CCR1, CCR2, CCR3, or CCR5 (e.g., MCP-1, MCP-2, MCP-3, MCP-4, MCP-5, MIP-1α, MIP-1β, and/or MIP-2) can be provided in the tissue of the mammalian subject to be treated by introducing an agent into target cells that causes, increases, and/or upregulates expression of at least one of chemokines ligands (e.g., MCP-1, MCP-2, MCP-3, MCP-4, MCP-5, MIP-1α, MIP-1β, and/or MIP-2) from the target cells. The target cells can include cells of the tissue to be treated as well as ex vivo cells (e.g., cardiofibroblasts) that are transplanted into the tissue to be treated following introduction of the agent. The cultured cells can be transplanted to the tissue being treated by well-known cell transplant techniques. For example, a suspension of cultured cells can be injected using a tuberculin syringe into the tissue being treated of the mammalian subject.

The ex vivo cells can be autologous or allogenic to the tissue of the mammalian subject being treated. Where the target cells are cells that are transplanted into the tissue to be treated, the target cell can be same cell type as the cells of the tissue being treated or a different cell type.

By way of example, where the tissue to be treated is infarcted myocardium the cells that are transplanted into the tissue to be treated can include cultured heart cells, skeletal myoblasts, fibroblasts (e.g., cardiofibroblasts), smooth muscle cells, and bone marrow derived cells. These cells can be harvested from the subject to be treated (i.e., autologous cells) and cultured prior to transplantation. Autologous cells can increase the biocompatibility of the cells upon transplantation and minimize the likelihood of rejection.

Examples of cells that can be transplanted into the infarcted myocardium include skeletal myoblasts. Myoblasts maintain the regenerative potential of skeletal muscle, during periods of stress, proliferate and differentiate into myotubes, eventually forming muscle fibers capable of contracting. Myoblasts implanted into myocardium undergo myotube formation, withdraw from cell cycle, and remain viable. Functional studies have shown an improvement in regional contractility and compliance after myoblast implantation into the myocardium.

Skeletal myoblasts can be readily harvested under the basal membrane of muscular fibers, cultured to scale up the cell line, and then transplanted into infarcted myocardium. For example, in a murine subject, skeletal myoblasts can be harvested from the hind limbs of the subject, cultured, and then transplanted into the infarcted myocardium of the subject.

Other examples of cell that can advantageously transplanted to infarcted myocardium includes cardiac fibroblast (i.e., cardiofibroblasts). Cardiofibroblasts are readily compatible with myocardial and can be readily transfected to express the chemokine of interest.

The cultured cells can be transplanted in the infarcted myocardium by, for example, injecting a suspension of the cultured cells using a tuberculin syringe into the infarcted myocardial tissue.

The agent that is introduced into the target cells can comprise natural or synthetic nucleic acids (e.g., MCP-1, MCP-2, MCP-3, MCP-4, MCP-5, MIP-1α, MIP-1β, and/or MIP-2 nucleic acids) that are incorporated into recombinant nucleic acid constructs, typically DNA constructs, capable of introduction into and replication in the cell. Such a construct preferably includes a replication system and sequences that are capable of transcription and translation of a polypeptide-encoding sequence in a given target cell.

Other agents can also be introduced into the target cells to cause expression of the chemokine ligands from the target cells. For example, agents that increase the transcription of a gene encoding MCP-1, MCP-2, MCP-3, MCP-4, MCP-5, MIP-1α, MIP-1β, and/or MIP-2 increase the translation of an mRNA encoding MCP-1, MCP-2, MCP-3, MCP-4, MCP-5, MIP-1α, MIP-1β, and/or MIP-2, and/or those that decrease the degradation of an mRNA encoding MCP-1, MCP-2, MCP-3, MCP-4, MCP-5, MIP-1α, MIP-1β, and/or MIP-2 could be used to increase MCP-1, MCP-2, MCP-3, MCP-4, MCP-5, MIP-1α, MIP-1β, and/or MIP-2 levels. Increasing the rate of transcription from a gene within a cell can be accomplished by introducing an exogenous promoter upstream of the gene encoding MCP-1, MCP-2, MCP-3, MCP-4, MCP-5, MIP-1α, MIP-1β, and/or MIP-2. Enhancer elements which facilitate expression of a heterologous gene may also be employed.

A preferred method of introducing the agent into a target cell involves using gene therapy. Gene therapy refers to gene transfer to express a therapeutic product from a cell in vivo or in vitro. Gene therapy in accordance with the present invention can be used to express the chemokine ligand (e.g., MCP-1, MCP-2, MCP-3, MCP-4, MCP-5, MIP-1α, MIP-1β, and/or MIP-2) from a target cell in vivo or in vitro.

One method of gene therapy uses a vector including a nucleotide encoding a chemokine ligands to at least one of CCR1, CCR2, CCR3, or CCR5 (e.g., MCP-1 MCP-2, MCP-3, MCP-4, MCP-5, MIP-1α, MIP-1β, and/or MIP-2). A "vector" (sometimes referred to as gene delivery or gene transfer "vehicle") refers to a macromolecule or complex of molecules comprising a polynucleotide to be delivered to a target cell, either in vitro or in vivo. The polynucleotide to be delivered may comprise a coding sequence of interest in gene therapy. Vectors include, for example, viral vectors (such as adenoviruses ('Ad'), adeno-associated viruses (AAV), and retroviruses), liposomes and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors, which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use in the present invention include viral vectors, lipid based vectors and other vectors that are capable of delivering a nucleotide according to the present invention to the target cells. The vector can be a targeted vector, especially a targeted vector that preferentially binds to specific cell types, such as cardiomyocytes. Preferred viral vectors for use in the invention are those that exhibit low toxicity to a target cell and induce production of therapeutically useful quantities of the chemokine ligands (e.g., MCP-1, MCP-2, MCP-3, MCP-4, MCP-5, MIP-1α, MIP-1β, and/or MIP-2) in a tissue-specific manner.

Presently preferred viral vectors are derived from adenovirus (Ad) or adeno-associated virus (AAV). Both human and non-human viral vectors can be used but preferably the recombinant viral vector is replication-defective in humans. Where the vector is an adenovirus, it preferably comprises a polynucleotide having a promoter operably linked to a gene encoding, for example, the MCP-1, MCP-2, MCP-3, MCP-4, MCP-5, MIP-1α, MIP-1β, and/or MIP-2 and is replication-defective in humans.

Adenovirus vectors are desired for use in the invention because they (1) are capable of highly efficient gene expression in target cells and (2) can accommodate a relatively large amount of heterologous (non-viral) DNA. An example of a recombinant adenovirus is a "gutless, "high-capacity", or "helper-dependent" adenovirus vector. Such a vector features, for example, (1) the deletion of all or most viral-coding sequences (those sequences encoding viral proteins), (2) the viral inverted terminal repeats (ITRs) which are sequences required for viral DNA replication, (3) up to 28-32 kb of "exogenous" or "heterologous" sequences (e.g., sequences encoding MCP-1, MCP-2, MCP-3, MCP-4, MCP-5, MIP-1α, MIP-1β, and/or MIP-2), and (4) the viral DNA packaging sequence which is required for packaging of the viral genomes into infectious capsids. For specifically myocardial cells, variants of such recombinant adenoviral vectors can contain tissue-specific (e.g., cardiomyoctye) enhancers and promoters operably linked to a chemokine ligand gene (e.g., MCP-1, MCP-2, MCP-3, MCP-4, MCP-5, MIP-1α, MIP-1β, and/or MIP-2 gene).

AAV-based vectors are advantageous because they exhibit high transduction efficiency of target cells and can integrate into the target genome in a site-specific manner. Use of recombinant AAV vectors is discussed in detail in Tal, J., J. Biomed. Sci. 7:279-291, 2000 and Monahan and Samulski, Gene Therapy 7:24-30, 2000. A preferred AAV vector comprises a pair of AAV inverted terminal repeats which flank at least one cassette containing a tissue (e.g., myocardium)—or cell (e.g., cardiomyocyte or cardiofibroblast)—specific promoter operably linked to at least one of a MCP-1, MCP-2, MCP-3, MCP-4, MCP-5, MIP-1α, MIP-1β, and/or MIP-2 nucleic acid. The DNA sequence of the AAV vector, including the ITRs, the promoter and MCP-1, MCP-2, MCP-3, MCP-4, MCP-5, MIP-1α, MIP-1β, and/or MIP-2 gene may be integrated into the target genome.

Other viral vectors that can be use in accordance with the present invention include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid. A preferred HSV vector is one that: (1) is engineered from HSV type I, (2) has its IE genes deleted, and (3) contains a tissue-specific (e.g., myocardium) promoter operably linked to at least one of a MCP-1, MCP-2, MCP-3, MCP-4, MCP-5, MIP-1α, MIP-1β, and/or MIP-2 nucleic acid. HSV amplicon vectors may also be useful in various methods of the invention. Typically, HSV amplicon vectors are approximately 15 kb in length, and possess a viral origin of replication and packaging sequences.

Retroviruses, such as C-type retroviruses and lentiviruses, can also be used in the invention. The structure and life cycle of retroviruses makes them ideally suited to be gene-transfer vehicles since (i) the majority of sequences coding for their structural genes are deleted and replaced by the gene(s) of interest which are transcribed under control of the retroviral regulatory sequences within its long terminal repeat (LTR) region and (ii) they replicate through a DNA intermediate that integrates into the host genome. Although the sites of integration appear to be random with respect to the host genome, the provirus integrates with a defined structure in low copy number.

Retroviruses can be RNA viruses; i.e., the viral genome is RNA. This genomic RNA is, however, reverse transcribed into a DNA intermediate which is integrated very efficiently into the chromosomal DNA of infected cells. This integrated DNA intermediate is referred to as a provirus. The retroviral genome and the proviral DNA have three genes: the gag, the pol and the env, which are flanked by two long terminal repeat (LTR) sequences. The gag gene encodes the internal structural (nucleocapsid) proteins, the pol gene encodes the RNA-directed DNA polymerase (reverse transcriptase); and the env gene encodes viral envelope glycoproteins. The 5' and 3' LTRs serve to promote transcription and polyadenylation of virion RNAs.

Adjacent to the 5' LTR are sequences necessary for reverse transcription of the genome (the tRNA primer binding site) and for efficient encapsidation of viral RNA into particles (the Psi site). Mulligan, R. C., In: Experimental Manipulation of Gene Expression, M. Inouye (ed). Proceedings of the National Academy of Sciences, U.S.A. 81:6349-6353 (1984).

In order to generate a viral particle containing the recombinant genome, it is necessary to develop cell lines that provide packaging "help". To accomplish this, a plasmid(s), encoding, for example, the retroviral structural genes gag, pol, and env, is introduced into an otherwise untransformed tissue cell line by conventional calcium-phosphate-mediated DNA transfection, Wigler, et al., Cell 11:223 (1977). This plasmid-containing cells are referred to as a "packaging cell line." These plasmid containing packaging cell lines can be maintained as such or a replication incompetent retroviral vector can be introduced into the cell's genome. In the latter case, the genomic RNA generated by the vector construct combines with the constitutively expressed retroviral structural proteins of the packaging line, resulting in the release of retroviral particles into the culture medium. A stable cell line containing the structural gene sequences of the retroviruses is a retroviral "producer cell line."

Retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and a nucleic acid, such as an MCP-1, MCP-2, MCP-3, MCP-4, MCP-5, MIP-1α, MIP-1β, and/or MIP-2 nucleic acid. In methods of delivery to an infarcted myocardium, it may also encode a ligand to a myocardial specific receptor.

Additional retroviral vectors that may be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells. They are also highly efficient at transducing human epithelial cells.

Lentiviral vectors for use in the invention may be derived from human and non-human (including SIV) lentiviruses. Preferred lentiviral vectors include nucleic acid sequences required for vector propagation as well as a tissue-specific promoter (e.g., myocardium) operably linked to a MCP-1, MCP-2, MCP-3, MCP-4, MCP-5, MIP-1α, MIP-1β, and/or MIP-2 gene. These former may include the viral LTRs, a primer binding site, a polypurine tract, att sites, and an encapsidation site.

A lentiviral vector may be packaged into any suitable lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN), might also be used in the invention. Use of alphaviruses is described in Lundstrom, K., Intervirology 43:247-257, 2000 and Perri et al., Journal of Virology 74:9802-9807, 2000. Alphavirus vectors typically are constructed in a format known as a replicon. A replicon may contain (1) alphavirus genetic elements required for RNA replication, and (2) a heterologous nucleic acid, such as one encoding a MCP-1, MCP-2, MCP-3, MCP-4, MCP-5, MIP-1α, MIP-1β, and/or MIP-2 nucleic acid. Within an alphavirus replicon, the heterologous nucleic acid may be operably linked to a tissue-specific (e.g., myocardium) promoter or enhancer.

Recombinant, replication-defective alphavirus vectors are advantageous because they are capable of high-level heterologous (therapeutic) gene expression, and can infect a wide target cell range. Alphavirus replicons may be targeted to specific cell types (e.g., cardiomyocytes and/or cardiofibroblasts) by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell. A preferred alphavirus vector or replicon is non-cytopathic.

In many of the viral vectors compatible with methods of the invention, more than one promoter can be included in the vector to allow more than one heterologous gene to be expressed by the vector. Further, the vector can comprise a sequence which encodes a signal peptide or other moiety which facilitates the secretion of a chemokine ligand gene product, such as a MCP-1, MCP-2, MCP-3, MCP-4, MCP-5, MIP-1α, MIP-1β, and/or MIP-2 gene product, from the target cell.

To combine advantageous properties of two viral vector systems, hybrid viral vectors may be used to deliver a nucleic acid, such as a MCP-1, MCP-2, MCP-3, MCP-4, MCP-5, MIP-1α, MIP-1β, and/or MIP-2 nucleic acid, to a target tissue (e.g., myocardium). Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000. Retroviral genomes contained within an adenovirus may integrate within the target cell genome and effect stable gene expression (e.g., MCP-1, MCP-2, MCP-3, MCP-4, MCP-5, MIP-1α, MIP-1β, and/or MIP-2 gene expression).

Other nucleotide sequence elements which facilitate expression of the chemokine ligand gene (e.g., MCP-1, MCP-2, MCP-3, MCP-4, MCP-5, MIP-1α, MIP-1β, and/or MIP-2 gene) and cloning of the vector are further contemplated. For example, the presence of enhancers upstream of the promoter or terminators downstream of the coding region, for example, can facilitate expression.

In accordance with another aspect of the present invention, a tissue-specific promoter, such as tissue-specific transcriptional control sequences of left ventricular myosin light chain-2 ($MLC_{2v}$) or myosin heavy chain (MHC), can be fused to a chemokine ligand gene (e.g., MCP-1, MCP-2, MCP-3, MCP-4, MCP-5, MIP-1α, MIP-1β, and/or MIP-2 gene). By fusing such tissue specific promoter within the adenoviral construct, transgene expression is limited to ventricular cardiomyocytes. The efficacy of gene expression and degree of specificity provided by tissue specific promoters can be determined, using the recombinant adenoviral system of the present invention. Cardiac-specific (i.e., myocardial tissue specific) expression is well known in the art. (J. Biol. Chem., 267:15875-15885, 1992). Other promoters, such as the troponin-C promoter, can also be used.

The use of tissue specific promoters directed to cardiomyocytes alone (i.e., without concomitant expression in endothelial cells, smooth muscle cells, and fibroblasts within the heart) when delivering the chemokine ligand gene (e.g., MCP-1, MCP-2, MCP-3, MCP-4, MCP-5, MIP-1α, MIP-1β, and/or MIP-2 gene) in vivo provides adequate expression of chemokine ligand for therapeutic treatment. Limiting expression to the cardiomyocytes also has advantages regarding the utility of gene transfer for the treatment of CHF. In addition, cardiomyocytes would likely provide the longest transgene expression since the cells do not undergo rapid turnover; expression would not therefore be decreased by cell division and death as would occur with endothelial cells. Endothelial-specific promoters are already available for this purpose (Lee, et al., J. Biol. Chem., 265:10446-10450, 1990).

In addition to viral vector-based methods, non-viral methods may also be used to introduce the chemokine ligand gene (e.g., MCP-1, MCP-2, MCP-3, MCP-4, MCP-5, MIP-1α, MIP-1β, and/or MIP-2 gene) into a target cell. A review of non-viral methods of gene delivery is provided in Nishikawa and Huang, Human Gene Ther. 12:861-870, 2001. A preferred non-viral gene delivery method according to the invention employs plasmid DNA to introduce a chemokine ligand nucleic acid (e.g., MCP-1, MCP-2, MCP-3, MCP-4, MCP-5, MIP-1α, MIP-1β, and/or MIP-2 nucleic acid) into a cell. Plasmid-based gene delivery methods are generally known in the art.

Synthetic gene transfer molecules can be designed to form multimolecular aggregates with plasmid DNA (e.g., harboring a MCP-1, MCP-2, MCP-3, MCP-4, MCP-5, MIP-1α, MIP-1β, and/or MIP-2 coding sequence operably linked to a myocardium-specific promoter). These aggregates can be designed to bind to a target cell (e.g., cardiomyocyte).

Cationic amphiphiles, including lipopolyamines and cationic lipids, may be used to provide receptor-independent nucleic acid (e.g., MCP-1, MCP-2, MCP-3, MCP-4, MCP-5, MIP-1α, MIP-1β, and/or MIP-2 nucleic acid) transfer into target cells (e.g., cardiomyocytes). In addition, preformed cationic liposomes or cationic lipids may be mixed with plasmid DNA to generate cell-transfecting complexes. Methods involving cationic lipid formulations are reviewed in Felgner et al., Ann. N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

Methods that involve both viral and non-viral based components may be used according to the invention. For example, an Epstein Barr virus (EBV)-based plasmid for therapeutic gene delivery is described in Cui et al., Gene Therapy 8:1508-1513, 2001. Additionally, a method involving a DNA/ligand/polycationic adjunct coupled to an adenovirus is described in Curiel, D. T., Nat. Immun. 13:141-164, 1994.

Vectors that encode the expression of the chemokine ligands to at least one of CCR1, CCR2, CCR3, or CCR5 (e.g., MCP-1, MCP-2, MCP-3, MCP-4, MCP-5, MIP-1α, MIP-1β, and/or MIP-2) can be delivered to the target cell in the form of an injectable preparation containing pharmaceutically acceptable carrier, such as saline, as necessary. Other pharmaceutical carriers, formulations and dosages can also be used in accordance with the present invention.

Where the target cell comprises a cell of the tissue to be treated (e.g., infarcted myocardium), the vector can be delivered by direct intracoronary injection using a tuberculin syringe under fluoroscopic guidance, at an amount sufficient for the chemokine ligand (e.g., MCP-1, MCP-2, MCP-3, MCP-4, MCP-5, MIP-1α, MIP-1β, and/or MIP-2) to be expressed to a degree which allows for highly effective therapy. By injecting the vector directly into the tissue to be treated (e.g., infarcted myocardial tissue) it is possible to target the gene rather effectively, and to minimize loss of the recombinant vectors.

This type of injection enables local transfection of a desired number of cells, (e.g., cardiomyocytes), in the effected tissue (e.g., myocardium), thereby maximizing therapeutic efficacy of gene transfer, and minimizing the possibility of an inflammatory response to viral proteins. For example, a cardiomyocyte-specific promoter may be used, for example, to securely enable expression limited to the cardiomyocytes. Thus, delivery of the transgenes in this matter may result in targeted gene expression in, for example, the cells of the left ventricle. Other techniques well known in the art can also be used for transplanting the vector to the target cells of the infarcted myocardium.

Where the target cell is a cultured cell that is later transplanted into the infarcted myocardium, the vectors can be delivered by direct injection into the culture medium. The nucleic acids (e.g., MCP-1, MCP-2, MCP-3, MCP-4, MCP-5, MIP-1α, MIP-1β, and/or MIP-2 nucleic acid) transfected into cells may be operably linked to any suitable regulatory sequence, including a tissue specific promoter (e.g., myocardium) and enhancer.

The transfected target cells can then be transplanted to the infarcted myocardium by well known transplantation techniques, such as by direct intracoronary injection using a tuberculin syringe. By first transfecting the target cells in vitro and then transplanting the transfected target cells to the infarcted myocardium, the possibility of inflammatory response in the infarcted myocardium is minimized compared to direct injection of the vector into the infarcted myocardium.

The chemokine ligands to at least one of CCR1, CCR2, CCR3, or CCR5 (e.g., MCP-1, MCP-2, MCP-3, MCP-4, MCP-5, MIP-1α, MIP-1β, and/or MIP-2) of the present invention may be expressed for any suitable length of time within the target cell, including transient expression and stable, long-term expression. In a preferred embodiment, the chemokine ligands will be expressed in therapeutic amounts for a suitable and defined length of time.

A therapeutic amount is an amount, which is capable of producing a medically desirable result in a treated animal or human. As is well known in the medical arts, dosage for any one animal or human depends on many factors, including the subject's size, body surface area, age, the particular composition to be administered, sex, time and route of administration, general health, and other drugs being administered concurrently. Specific dosages of proteins, nucleic acids, or small molecules) can be determined readily determined by one skilled in the art using the experimental methods described below.

The chemokine expression may be transient or may be long-term, as is the case where the tissue to be treated (e.g., infarcted myocardium) is transfected with an MCP-1, MCP-2, MCP-3, MCP-4, MCP-5, MIP-1α, MIP-1β, and/or MIP-2 encoding vector or where a cell that is transfected with an MCP-1, MCP-2, MCP-3, MCP-4, MCP-5, MIP-1α, MIP-1β, and/or MIP-2 encoding vector is transplanted to the tissue to be treated (e.g., infarcted myocardium.

Long term expression of the chemokine ligand is advantageous because it allows the concentration of stem cells to be increased at a time remote from surgery or a procedure that transplants transfected target cells. Additionally, long term or chronic up-regulation of the chemokine ligand to CCR1, CCR2, CCR3, and/or CCR5 would allow multiple attempts at increasing the stem cell concentration in the peripheral blood. Further, chronic up-regulation in the chemokine ligand expression causes long term homing of stem cells into the tissue to be treated (e.g., infarcted myocardial tissue) from the peripheral blood without the need of stem cell mobilization agent.

The chemokine ligand to at least one of CCR1, CCR2, CCR3, or CCR5 can induce migration of stem cells that express or are induced to express at least one of CCR1, CCR2, CCR3, or CCR5, such as MSCs, MAPCs, and/or other stem cells, from the peripheral blood to the tissue being treated. The stem cells can be provided in the peripheral blood of the tissue being treated by directly injecting the stem cells into the tissue or tissue proximate the tissue being treated by using, for example, a tuberculin syringe. The stem cells can also be provided in the peripheral blood by venous or arterial infusion of the stem cells into the mammalian subject to be treated. The infused stem cells can then be induced to migrate to the tissue being treated by the MCP-1, MCP-2, MCP-3, MCP-4, MCP-5, MIP-1α, MIP-1β, and/or MIP-2 provided in the tissue.

The stem cells that express or are induced to express at least one of CCR1, CCR2, CCR3, or CCR5 can be injected or infused into the mamalian subject after providing the chemokine ligand (e.g., MCP-1, MCP-2, MCP-3, MCP-4, MCP-5, MIP-1α, MIP-1β, and/or MIP-2) in the tissue being treated. The stem cells, however, can be administered before providing the chemokine ligand (e.g., MCP-1, MCP-2, MCP-3, MCP-4, MCP-5, MIP-1α, MIP-1β, and/or MIP-2) in the tissue being treated.

In an aspect of the invention, the stem cells that express or are induced to express at least one of CCR1, CCR2, CCR3, or CCR5 can be injected or infused into the mamalian subject by multiple infusions. By way of example, the half-life of MSC in the blood stream following intravenous infusion is typically short (e.g., less than about 1 hour). Therefore, by provided in serial infusions of MSCs into mammals provided with the chemokine ligand (e.g., MCP-1, MCP-2, MCP-3, MCP-4, MCP-5, MIP-1α, MIP-1β, and/or MIP-2) in the tissue to be treated leads to greater MSC engraftment.

Alternatively, the stem cells can be provided in the tissue to be treated by administering an agent to induce mobilization of stem cells, such as MSCs and/or MAPCs, to the peripheral blood of the subject. The stems cells can be mobilized to the peripheral blood of the subject to increase stem cell concentration in peripheral subject using a number of agents. For example, to increase the number of stem cells in the peripheral blood of a mammalian subject, an agent that causes a pluripotent stem cell to mobilize from the bone marrow can be administered to the subject. A number of such agents are known and include cytokines, such as granulocyte-colony stimulating factor (G-CSF), granulocyte-macrophage colony stimulating factor (GM-CSF), interleukin (IL)-7, IL-3, IL-12, stem cell factor (SCF), and flt-3 ligand; chemokines such as IL-8, Mip-1α, and Groβ, and the chematherapeutic agents of cylcophosamide (Cy) and paclitaxel. These agents differ in their time frame to achieve stem cell mobilization, the type of stem cell mobilized, and efficiency.

The mobilizing agent can be administered by direct injection of the mobilizing agent into the subject. Preferably, the mobilizing agent is administered after the MCP-1, MCP-2, MCP-3, MCP-4, MCP-5, MIP-1α, MIP-1β, and/or MIP-2 is provided in the tissue being treated. The mobilizing agent, however, can be administered before the MCP-1, MCP-2, MCP-3, MCP-4, MCP-5, MIP-1α, MIP-1β, and/or MIP-2 is provided in the tissue being treated.

The chemokine ligands to at least one of CCR1, CCR2, CCR3, or CCR5 can be provided in any tissue or organ system and/or for potentially any cellular therapy or therapeutic application where it is desirable to induce migration of MSCs, MAPCs, and/or other stem cells to expand, repopulate, preserve, and/or regenerate tissue and/or organ systems. In accordance with an aspect of the invention, the chemokine ligands to at least one of CCR1, CCR2, CCR3, or CCR5 can be used in a method of myocardium regeneration of ischemic regions of the heart (or skeletal muscle in the case of peripheral vascular tissue). The method of the can be used to treat ischemic cardiomyopathy at a time remote (i.e., weeks) from myocardial infarction.

The method includes mobilizing and directing migration of stem cells that express or are induced express at least one of CCR1, CCR2, CCR3, or CCR5, such as MSCs and/or MAPCs, to infarcted myocardium within a mammalian subject. The infarcted myocardium can include the infarcted myocardial tissue, the myocardial tissue about the periphery of the infarcted myocardial tissue, and both the infarcted myocardial tissue and myocardial tissue about the periphery of the infarcted myocardial tissue.

At a time remote from myocardial infarction, stem cells that express or are induced to express at least one of CCR1, CCR2, CCR3, or CCR5, such as MSCs, MAPCs, and/or other stem cells can be induced to traffic the infarcted myocardium by increasing the concentration of, for example, MCP-1, MCP-2, MCP-3, MCP-4, MCP-5, MIP-1α, MIP-1β, and/or MIP-2 in infarcted myocardial tissue from a first concentration to a second concentration. The first concentration of MCP-1, MCP-2, MCP-3, MCP-4, MCP-5, MIP-1α, MIP-1β, and/or MIP-2 can be the concentration of MCP-1, MCP-2, MCP-3, MCP-4, MCP-5, MIP-1α, MIP-1β, and/or MIP-2 protein typically found in an infarcted myocardium at a time remote (i.e., weeks) from the myocardial infarction. The second concentration of MCP-1, MCP-2, MCP-3, MCP-4, MCP-5, MIP-1α, MIP-1β, and/or MIP-2 protein can be substantially greater than the first concentration of MCP-1, MCP-2, MCP-3, MCP-4, MCP-5, MIP-1α, MIP-1β, and/or MIP-2 protein. The concentration of MCP-1, MCP-2, MCP-3, MCP-4, MCP-5, MIP-1α, MIP-1β, and/or MIP-2 protein can be increased in the infarcted myocardium by administering or up-regulating the expression of MCP-1, MCP-2, MCP-3, MCP-4, MCP-5, MIP-1α, MIP-1β, and/or MIP-2 protein within the infarcted myocardium from the amount of MCP-1, MCP-2, MCP-3, MCP-4, MCP-5, MIP-1α, MIP-1β, and/or MIP-2 typically found in the infarcted myocardium at a time remote from the myocardial infarction.

By inducing stem cells to the infarcted myocardium, the infarcted myocardial tissue can be regenerated because there will be a greater number of stem cells in the infarcted myocardium that can differentiate into cells, which can repopulate (i.e., engraft) and partially or wholly restore the normal function of the infarcted myocardium.

The method of the present invention further includes a step of increasing the concentration (i.e., number) of stems cells that express or are induced to express at least one of CCR1, CCR2, CCR3, or CCR5, such as MSCs, MAPCs, and/or other stem cells, in the peripheral blood from a first concentration to a second concentration substantially greater than the first concentration. The first concentration of stem cells can be the concentration of stem cells typically found in the peripheral blood at a time remote from the myocardial infarction. The concentration of stem cells in the peripheral blood can be increased while the concentration of MCP-1, MCP-2, MCP-3, MCP-4, MCP-5, MIP-1α, MIP-1β, and/or MIP-2 protein in the infarcted myocardium is increased. The concentration of stem cells in the peripheral blood can be increased either before or after the MCP-1, MCP-2, MCP-3, MCP-4, MCP-5, MIP-1α, MIP-1β, and/or MIP-2 protein expression is up-regulated in the infarcted myocardium.

The MSCs, MAPCs, and/or other stem cells that express or are induced to express at least one of CCR1, CCR2, CCR3, or CCR5 used to regenerate myocardial structures can be delivered to the infarcted myocardium by directly injecting the MSCs, MAPCs, and/or other stem cells used to regenerate myocardial structures into the infarcted myocardial tissue or myocardial tissue proximate the infarction by using, for example, a tuberculin syringe. Alternatively, the stem cells, such as MSCs, MAPCs, and/or other stem cells can be delivered to the infarcted myocardial tissue by venous or arterial infusion into the mammalian subject to be treated. The infusion of the MSCs, MAPCs, and/or other stem cells used to regenerate myocardial structures can be performed soon (e.g., about 1 day) or remote (e.g., weeks) after the myocardial infarction. Moreover, the MSCs, MAPCs, and/or other stem cells used to regenerate myocardial structures can be infused at multiple times during the course of treatment.

The stem cells, such as MSCs, MAPCs, and/or other stem cells, induced the increased concentration of MCP-1, MCP-2, MCP-3, MCP-4, MCP-5, MIP-1α, MIP-1β, and/or MIP-2 protein to the infarcted myocardium facilitate myocardial regeneration and can provide a substantial increase in left ventricular function.

It will be appreciated, that although the use of chemokine ligands to at least one of CCR1, CCR2, CCR3, or CCR5 for inducing stem cells that express or are induced to express at least one of CCR1, CCR2, CCR3, or CCR5, such as MSC and/or MAPCs, to tissue being treated is primarily described for treatment of an acute myocardial infarction or congestive heart failure, the chemokine ligands to at least one of CCR1, CCR2, CCR3, or CCR5 can be used for other therapeutic applications where it is desirable to induce stem cells, such as MSCs, MAPCs, and/or other stem cells, for treatment. For example, the chemokine ligands to at least one of CCR1, CCR2, CCR3, or CCR5 and stem cells in accordance with the present invention can be used for the regeneration of hepatocytes to replace damaged liver tissue and restore liver function, in conjunction with marrow transplantation, for the regeneration of marrow following marrow ablation by chemotherapy and/or irradiation, for bone and/or cartilage reconstruction, for the correcting of muscle disorders (e.g., muscular dystrophy), as well as other therapeutic applications where tissue is regenerated or where MSCs, MAPCs, and/or other stems that express or are induced to express at least one of CCR1, CCR2, CCR3, or CCR5 are typically used.

EXAMPLES

The present invention is further illustrated by the following series of examples. The examples are provided for illustration and are not to be construed as limiting the scope or content of the invention in any way.

Introduction

MSC can differentiate into a number of organ specific cell types as well as modulate local microenvironment of injured tissues and modulate the immune system. Little is known about how stem cells traffic/home to injured tissue. Recently, a sub-population of MSC have been shown to express the SDF-1 chemokine receptor CXCR4, and some studies have suggested that this population, may therefore, home in response to SDF-1 expression. While intriguing, MSC themselves express SDF-1, and there is little precedent in the literature for a cell to migrate in response to a chemokine that they themselves secrete.

We have demonstrated that there is transient homing of hematopoietic stem cells to the heart following myocardial infarction. The transient nature of HSC homing is due to the transient expression of SDF-1. Since MSC have been shown to home to the heart following MI, we hypothesized that there are similarly chemokine(s) secreted by the myocardium that home MSC. To identify potential MSC homing factor(s), we implemented a gene array based strategy.

Materials and Methods

LAD Ligation:

The Animal Research Committee approved all animal protocols and all animals were housed in the AAALAC animal facility of the Cleveland Clinic Foundation. Ligation of the left anterior descending artery in Lewis rat was performed. Briefly Animals were anesthetized with intraperitoneal ketamine and xylazine and intubated and ventilated with room air at 80 breaths per minute using a pressure-cycled rodent ventilator (RSP 1002, Kent Scientific Corp, Torrington, Conn.). Anterior wall myocardial infarction was induced by direct ligation of the left anterior descending (LAD) artery with the aid of a surgical microscope (M500, Leica™ Microsystems, Bannockburn, Ill.).

Cell Preparation and Delivery:

Rat bone marrow was isolated by flushing the femurs with 0.6 ml DMEM (GIBCO, Invitrogen, Carlsbad, Calif.). Clumps of bone marrow were gently minced with a 20-gauge needle. Cells were separated by Percoll density gradient. The cells were centrifuged for 10 minutes at 260 g and washed with three changes of PBS with 100 U/ml penicillin/100 g/ml streptomycin (Invitrogen, Carlsbad, Calif.). The washed cells were then re-suspended and plated in DMEM-LG (GIBCO, Invitrogen, Carlsbad, Calif.) with 10% FBS and 1% antibiotic and antimycotic (GIBCO, Invitrogen, Carlsbad, Calif.). The cells were incubated at 37° C. Non-adherent cells were removed by replacing the medium after 3 days. Fourteen days later (passage 4) cells were harvested by incubation 0.05% trypsin and 2 mM EDTA (Invitrogen®, Carlsbad, Calif.) for 5 minutes. MSC Cultures were depleted of $CD45^+$ cells by negative selection using 10 µl each of primary PE-conjugated mouse anti-rat CD45 antibodies per $10^6$ cells (Vendor: BD Biosciences; Cat Number: 554878). PE-positive cells were negatively selected using the EasySep PE selection kit according to the manufacturer's instruction (Stem Cell technologies). The resulting MSC (passage 6-12) were used for our studies. Three days before infusion, the cells were freshly plated out at 1:3 ratio and incubated in complete medium with 10 μM BrdU (5-bromo 2-deoxyuridine) to label those cells in the S phase of the cell cycle. BrdU labeled MSC were harvested at $10^6$ cells/100 μl of PBS.

Rat cardiac fibroblasts were and stably transfected with rat MCP-3 expression vector or pcDNA3.1 (control vector). The expression of MCP-3 was confirmed by real-time PCR. Confluent cells were passaged and plated out at 1:2 to 1:3 dilutions until passage 11.

Real-Time PCR:

RT-PCR was performed following isolation of RNA from 6 million cells by using a Rneasy Mini Kit (Qiagen Inc., Valencia, Calif.) according to manufacturer instructions. Quantitative real-time PCR was performed by using the ABI Prism 7700 sequence detector (Applied Biosystems, Foster City, Calif.). The reaction mixture contained SYBR Green PCR master mix (Applied Biosystems, Foster City, Calif.), each primer at 300 nM, and 10 μl of cDNA. After activation of the AmpliTaq Gold (Applied Biosystems, Foster City, Calif.) for 10 minutes at 95° C., we carried out 45 cycles with each cycle consisting of 15 seconds at 95° C. followed by 1 minute at 60° C. The dissociation curve for each amplification was analyzed to confirm that there were no nonspecific PCR products. CXCR4 Primer Sequences: Forward: ATCATCTCCAAGCT-GTCACACTCC; Reverse: GTGATGGAGATCCACTTGT-GCAC Immunostaining:

Animals were sacrificed 72 h or 4 w following myocardial infarction. Tissues were fixed in formalin and embedded in paraffin blocks according to established protocols. Antigen retrieval was performed using 10 mM sodium citrate buffer (pH 6.0) and heat at 95° C. for 5 minutes. The buffer was replaced with fresh buffer and re-heated for an additional 5 minutes and then cooled for approximately 20 minutes. The slides were then washed in de-ionized water three times for 2 minutes each. Specimens were then incubated with 1% normal blocking serum in PBS for 60 minutes to suppress non-specific binding of IgG. Slides were then incubated for 60 minutes with the mouse anti-BrdU primary antibody (BD Biosciences, San Jose, Calif.). Optimal antibody concentration was determined by titration. Slides were then washed with phosphate buffered saline (PBS) and then incubated for 45 minutes with FITC-conjugated secondary antibody (Santa Cruz Biotechnology Inc., Santa Cruz, Calif.) diluted to 1.5 ug/ml in PBS with serum and incubated in a dark chamber. After washing extensively with PBS, coverslips were mounted with aqueous mounting medium (Vectashield Mounting Medium with DAPI, H-1200; Vector Laboratories, Burlingame, Calif.).

Confocal immunofluorescence Microscopy:

Tissue were analyzed using a upright spectral laser scanning confocal microscope (Model TCS-SP; Leica Microsystems, Heidelberg, Germany) equipped with blue argon (for DAPI), green argon (for Alexa Fluor 488) and red krypton (for Alexa Fluor 594) laser. Data was collected by sequential excitation to minimize "bleed-through". Image processing, analysis and the extent of co-localization were evaluated using the Leica Confocal software. Optical sectioning was averaged over four frames and the image size was set at $1024 \times 10^{24}$ pixels. There were no digital adjustments made to the images.

Western Protocol:

Cell extracts were prepared in 4× reducing Lamellae Buffer (200 mM Tris HCl (pH 6.8), 8% SDS, 0.1% Bromophenol Blue, 40% Glycerol). Sodium dodecyl sulfate (SDS) gels were prepared according to established protocols. Proteins were separated in a 10% SDS polyacrylamide gel. The blotting membrane was placed in 5% milk in 1×TBST (Tris Base-2.42 g, NaCl-8 g, 1M HCl-3.8 mL with pH to 7.5, Water-1 L, Tween 20-2 mL) for one hour and then probed with primary antibody (1:1000 in 5% Milk in 1×TBST) against phosphorylated Akt (Santa Cruz Biotechnology Inc., Santa Cruz, Calif.) followed by incubation with the peroxidase-conjugated anti-mouse secondary antibody (1:5000 in 1×TBST). Chemiluminescence (Amersham Biosciences UK Limited, Buckinghamshire, England) was used for visualization.

Echocardiography:

2D-echocardiography was performed at 2 and 5 weeks following LAD ligation and MSC transplantation using a 15 MHz linear array transducer interfaced with a Sequoia C256 and GE Vision 7. LV dimensions and wall thickness were quantified by digitally recorded 2D clips and M-mode images in a short axis view from the mid-LV just below the papillary muscles to allow for consistent measurements from the same anatomical location in different rats. The ultrasonographer was blinded to treatment group. Measurements were made by two independent blinded observers off-line using ProSolv echocardiography software. Measurements in each animal were made 6 times from 3 out of 5 randomly chosen M-mode clips recorded by an observer blinded to the treatment arm. Shortening fraction was calculated from the M-mode recordings. Shortening fraction (%)=(LVEDD−LVESD)/LVEDD× 100, where LVEDD=left ventricular end diastolic dimension and LVESD=left ventricular end systolic dimension.

Results

MSC Transiently Home to Injured Myocardium

Two million BrdU labeled MSC were infused into the tail vein of the rat at 1 or 14 d after LAD ligation. Three days following MSC infusion, the rats were killed and the heart harvested. MSC were quantified as the number of BrdU positive cells per $mm^2$. The data in FIG. 1 demonstrate that our MSC preparation transiently homes to the myocardium following acute myocardial infarction. One day after LAD ligation, a significant number of MSC was identified per unit area, where as 14 d after LAD ligation, the infusion of MSC did not result in significant MSC engraftment within the infarct zone.

Identification of Candidate MSC Homing Factors

Figure 2:
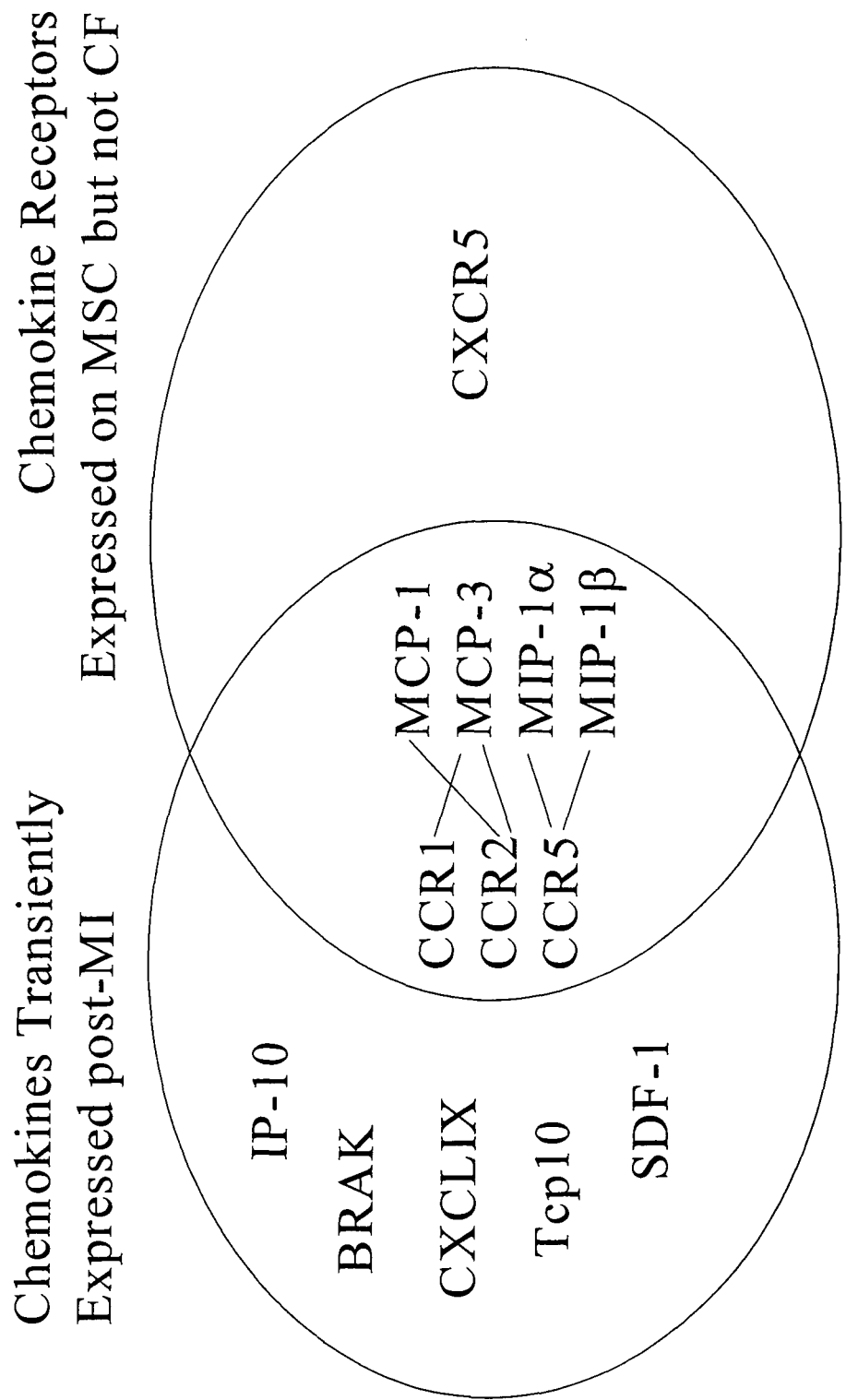
FIG. 2 is a graph comparing the chemokines transiently expressed post-myocardial infarction and the chemokine receptors expressed on MSC but not cardiofibroblasts (CF)

FIG. 2 depicts the strategy we implemented to identify candidate MSC homing factors, as well as the results. Using a chemokine and chemokine receptor array, we identified two distinct populations. The first was the population of chemokines that were expressed as early as 1 h after LAD ligation, and whose expression was gone by 10 d after LAD ligation (Circle on Left). The second population was made up of chemokine receptors that were expressed on MSC but not expressed on the surface of cardiac fibroblasts (Circle on Right). Candidate MSC homing factors were those chemokines that were contained in the Circle on the Left (transiently expressed by myocardial tissue after LAD ligation) that bound receptors that were contained in the Circle on the Left (expressed by MSC and not cardiac fibroblasts). As depicted in FIG. 2, only two families of chemokines were identified, the monocytes chemotractant proteins (1 and 3) via receptors CCR-1 and CCR-2 and MIP-1□ and □ via the receptor CCR-5.

Figure 3:
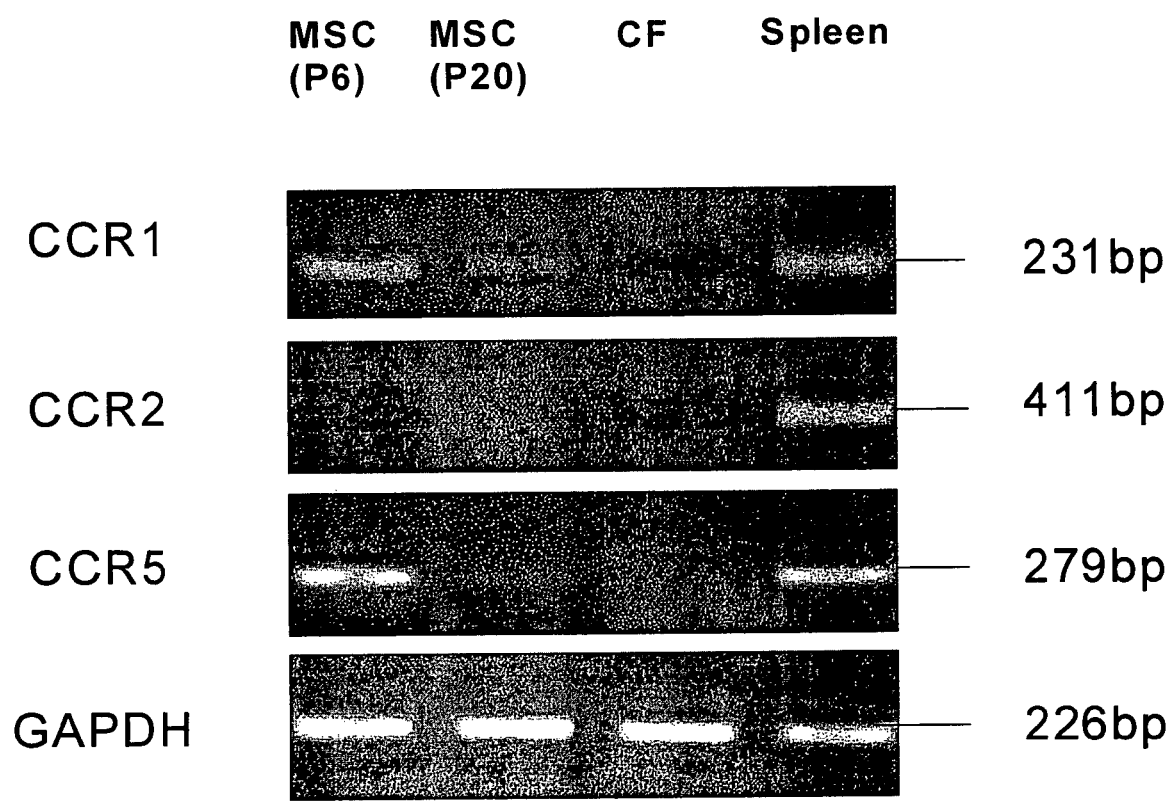
FIG. 3 illustrates expression of CCR1, CCR2, and CCR5 in MSCs, CF and rat spleen as determined by PCR.

In order to validate and refine the findings from our array studies, we performed PCR to further assess the presence of CCR1, CCR2 and CCR5. FIG. 3 shows PCR products from MSC, CF and rat Spleen (positive control). These results indicate that expression of CCR1 and CCR5 are significantly greater than CF in young MSC, and that the expression of CCR5 by MSC is lost over time.

Effect of MCP-3 Expression on MSC Homing

Based on the observation that (i) CCR2 expression appears to be maintained in MSC and (ii) the ability of MSC to home over time is not lost, we chose to focus on MCP-3. An additional pre-defined criterion for identifying an MSC homing factor is that MSC do not express the chemokine of interest. We performed real-time PCR analysis for MCP-3 expression in MSC and CF. The data shows that MSC do not express significant levels of MCP-3.

To test if MCP-3 can induce MSC homing, we transplanted control or MCP-3 expressing CF into the infarct border zone 1 month after LAD ligation. Three days later, we infused 2 million BrdU labeled MSC via the tail vein, and quantified MSC engraftment 3 days later. The data in FIG. 4 demonstrates that the re-establishment of MCP-3 expression in myocardial tissue restores the ability of myocardial tissue to home and engraft circulating MSC. While these data are consistent with MCP-3 having a role in MSC homing, the level of MSC engraftment was low relative to HSC engraftment in response to chronic SDF-1 expression in the same model.

Figure 4:
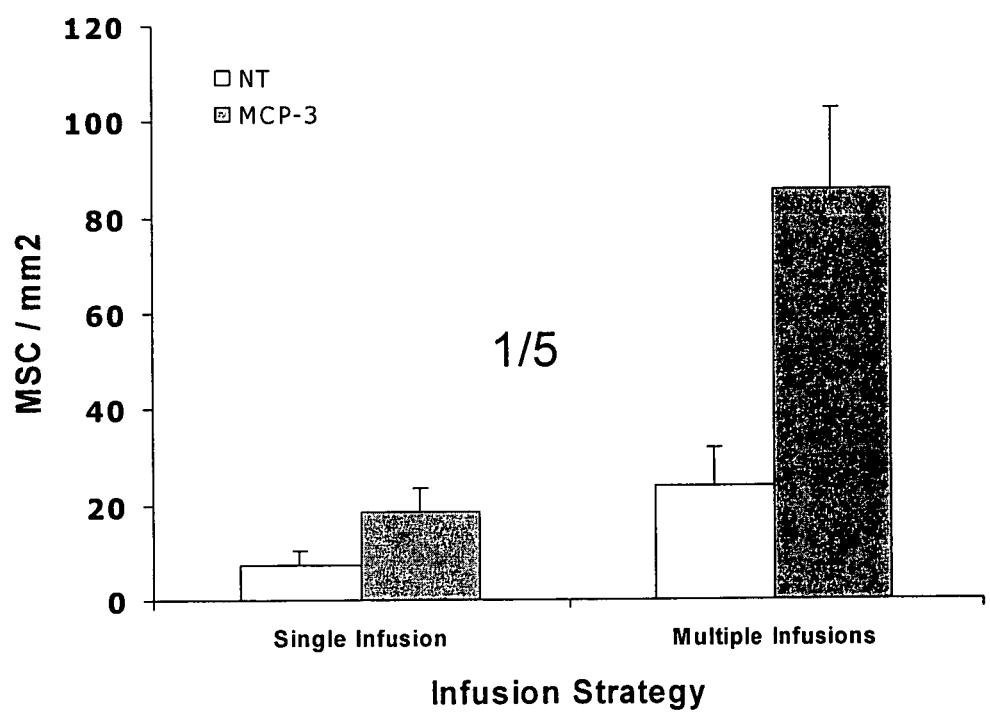
FIG. 4 is a graph comparing the number of MSCs per unit area in the infarct zone following a single infusion of MSCs and multiple infusions of MSCs for CFs expressing MCP-3 and CFs not expressing MCP-3.

We reasoned that one of the causes of the relatively low engraftment of MSC in response to MCP-3 was the fact that, unlike HSC, MSC are not constitutively released by the bone marrow, and that the half-life of MSC in the blood stream following intravenous infusion is short (<1 h). Therefore, we hypothesized that serial infusions of MSC into animals that were transplanted with MCP-3 expressing CF would lead to great MSC engraftment. The data in FIG. 4 show that following 6 intravenous infusions over 12 days of 1 million MSC per infusion there were significantly great MSC engrafted into the myocardium of animals that received MCP-3 expressing CF compared to control CF.

Effect of Re-Establishing MSC Homing on Cardiac Function

Figure 5B:
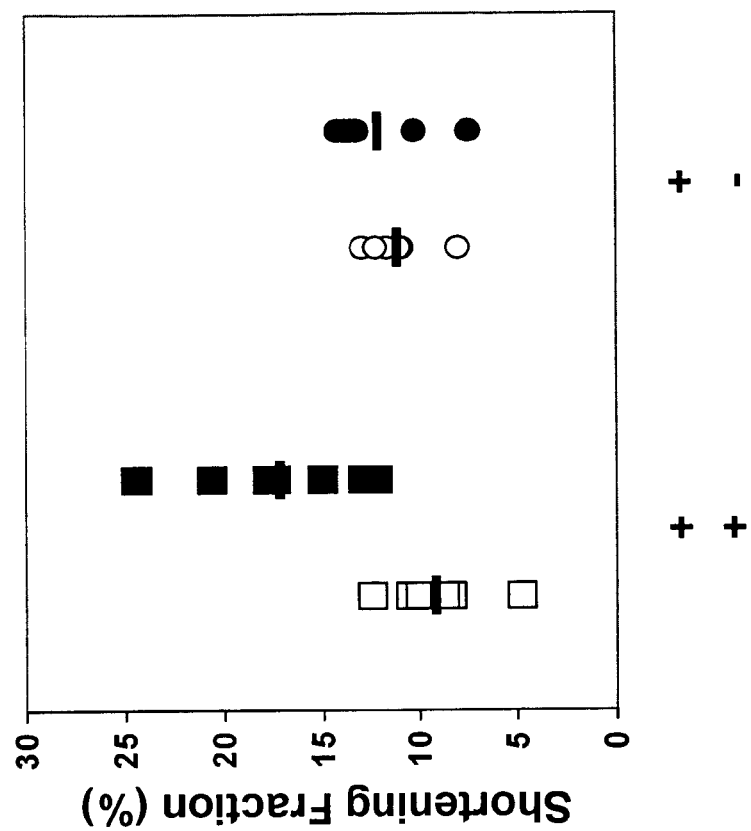
FIGS. 5a and 5b are graphs illustrating respectively LVEDD and shortening fraction of for rats receiving MCP-3 expressing CFs compared to control CFs.
Figure 5A:
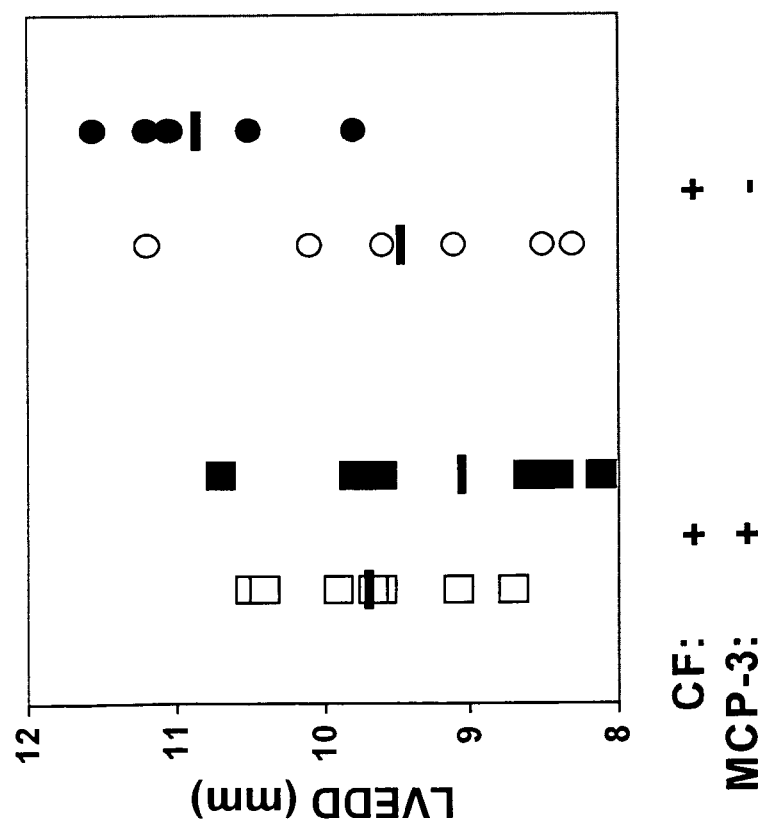

We transplanted control and MCP-3 expressing CF 1 month after LAD ligation. All animals then received 6 infusions of 1 million MSC per infusion every other day for 12 days beginning 3 days after CF transplantation. Cardiac function and dimensions were quantified by echocardiography 1 month after CF transplantation (2 months after MI). The data in FIG. 5b demonstrate that cardiac function as measured by shortening fraction was significantly increased in those animals that received MCP-3 expressing CF. No improvement in cardiac function was seen with CF transplantation. The animals that received MCP-3 expressing CF also had significantly shorter left ventricular end-diastolic dimension compared to those animals that received control CF (FIG. 5a).

From the above description of the invention, those skilled in the art will perceive improvements, changes and modifications. Such improvements, changes and modifications within the skill of the art are intended to be covered by the appended claims.

We claim:

1. A method of treating ischemic tissue in a subject comprising:
introducing directly into or locally expressing in the ischemic tissue monocyte chemotactic protein-3 (MCP-3), at an amount and for a length of time effective to induce homing of mesenchymal stem cells which are chemoattracted to MCP-3 from the peripheral blood of the ischemic tissue, wherein said local expression of MCP-3 in the ischemic tissue is obtained by administering an expression vector comprising a nucleic acid encoding for MCP-3 into the ischemic tissue; and
increasing the concentration of mesenchymal stem cells in the peripheral blood of the ischemic tissue being treated from a first concentration to a second concentration, wherein the mesenchymal stem cells are chemoattracted to the MCP-3 and engraft in the ischemic tissue being treated.

2. The method of claim 1, wherein the concentration of mesenchymal stem cells is increased by arterial or venous infusion of the mesenchymal stem cells.

3. The method of claim 2, wherein the mesenchymal stem cells express and/or are induced to express at least one of CCR1, CCR2, CCR3, or CCR5.

4. The method of claim 1, wherein the MCP-3 is locally expressed by introducing an expression vector into the tissue being treated, the expression vector comprising a nucleic acid encoding for the MCP-3.

5. A method of treating infarcted myocardial tissue at a time remote from the infarction comprising:
introducing directly into or locally expressing in the infarcted myocardial tissue monocyte chemotactic protein-3 (MCP-3), at an amount and for a length of time effective to induce homing of mesenchymal stem cells which are chemoattracted to MCP-3 from the peripheral blood of the infarcted myocardial tissue, wherein said local expression of MCP-3 in the infarcted myocardial tissue is obtained by administering an expression vector comprising a nucleic acid encoding for MCP-3 into the tissue; and
increasing the concentration of mesenchymal stem cells in the peripheral blood of the infarcted myocardial tissue being treated from a first concentration to a second concentration, wherein the mesenchymal stem cells are chemoattracted to the MCP-3 and engraft in the infarcted myocardial tissue being treated.

6. The method of claim 5, wherein the concentration of mesenchymal stem cells is increased by arterial or venous infusion of the mesenchymal stem cells.

7. The method of claim 6, wherein the stem cells express or are induced to express at least one of CCR1, CCR2, CCR3, or CCR5.

8. The method of claim 5, wherein the MCP-3 is locally expressed in the infarcted myocardial tissue being treated by introducing an expression vector into the infarcted myocardial tissue, the expression vector comprising a nucleic acid encoding for MCP-3.

9. The method of claim 6, wherein the mesenchymal stem cells are infused at multiple intervals following introducing or locally expressing MCP-3 in the infarcted myocardial tissue.

10. A method of inducing mesenchymal stem cells expressing a CCchemokine receptor-2 (CCR-2) in a subject to ischemic tissue of the subject, comprising:
introducing directly into or locally expressing in ischemic tissue of the subject monocyte chemotactic protein-3 (MCP-3), at an amount and for a length of time effective to induce homing of mesenchymal stem cells expressing CCR-2 from peripheral blood to the ischemic tissue, wherein said local expression of MCP-3 in the ischemic tissue is obtained by administering an expression vector comprising a nucleic acid encoding for MCP-3 into the ischemic tissue.

11. The method of claim 10, the MCP-3 is locally expressed by introducing directly into the ischemic tissue, an expression vector, the expression vector comprising a nucleic acid encoding MCP-3.

12. The method of 11, wherein the MCP-3 is locally expressed by injecting plasmid DNA encoding MCP-3 into the ischemic tissue.

13. The method of claim 10, wherein the MCP-3 is introduced directly into the ischemic tissue by direct injection of the MCP-3 into the ischemic tissue.

14. A method of inducing mesenchymal stem cells expressing a CCchemokine receptor-2 (CCR-2) in a subject to infarcted myocardial tissue of the subject, comprising:
introducing directly into or locally expressing in the infarcted myocardial tissue of the subject monocyte chemotactic protein-3 (MCP-3), at an amount and for a length of time effective to induce homing of mesenchymal stem cells expressing CCR-2 from the peripheral blood to the infarcted myocardial ischemic tissue, wherein said local expression of MCP-3 in the infarcted myocardial tissue is obtained by administering an expression vector comprising a nucleic acid encoding for MCP-3 into the tissue.

15. The method of claim 14, wherein the MCP-3 is locally expressed by introducing directly into the infarcted myocardial tissue an expression vector, the expression vector comprising a nucleic acid encoding MCP-3.

16. The method of 14, wherein the MCP-3 is locally expressed by injecting plasmid DNA encoding MCP-3 into the infarcted myocardial tissue.

17. The method of claim 14, wherein the MCP-3 is introduced directly into the infarcted myocardial tissue by direct injection of the MCP-3 into the infarcted myocardial tissue.

* * * * *

SEQUENCE LISTING

```
<160> NUMBER OF SEQ ID NOS: 16

<210> SEQ ID NO 1
<211> LENGTH: 99
<212> TYPE: PRT
<213> ORGANISM: Homo sapiens

<400> SEQUENCE: 1

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 2
<211> LENGTH: 99
<212> TYPE: PRT
<213> ORGANISM: Homo sapiens

<400> SEQUENCE: 2

Met Lys Val Ser Ala Ala Leu Leu Cys Leu Leu Leu Met Ala Ala Thr
1               5                   10                  15

Phe Ser Pro Gln Gly Leu Ala Gln Pro Asp Ser Val Ser Ile Pro Ile
            20                  25                  30
```

-continued

Thr Cys Cys Phe Asn Val Ile Asn Arg Lys Ile Pro Ile Gln Arg Leu
            35                  40                  45

Glu Ser Tyr Thr Arg Ile Thr Asn Ile Gln Cys Pro Lys Glu Ala Val
 50                  55                  60

Ile Phe Lys Thr Lys Arg Gly Lys Glu Val Cys Ala Asp Pro Lys Glu
 65                  70                  75                  80

Arg Trp Val Arg Asp Ser Met Lys His Leu Asp Gln Ile Phe Gln Asn
                85                  90                  95

Leu Lys Pro

<210> SEQ ID NO 3
<211> LENGTH: 99
<212> TYPE: PRT
<213> ORGANISM: Homo sapiens

<400> SEQUENCE: 3

Met Lys Ala Ser Ala Ala Leu Leu Cys Leu Leu Leu Thr Ala Ala Ala
 1               5                  10                  15

Phe Ser Pro Gln Gly Leu Ala Gln Pro Val Gly Ile Asn Thr Ser Thr
                20                  25                  30

Thr Cys Cys Tyr Arg Phe Ile Asn Lys Lys Ile Pro Lys Gln Arg Leu
            35                  40                  45

Glu Ser Tyr Arg Arg Thr Thr Ser Ser His Cys Pro Arg Glu Ala Val
 50                  55                  60

Ile Phe Lys Thr Lys Leu Asp Lys Glu Ile Cys Ala Asp Pro Thr Gln
 65                  70                  75                  80

Lys Trp Val Gln Asp Phe Met Lys His Leu Asp Lys Lys Thr Gln Thr
                85                  90                  95

Pro Lys Leu

<210> SEQ ID NO 4
<211> LENGTH: 98
<212> TYPE: PRT
<213> ORGANISM: Homo sapiens

<400> SEQUENCE: 4

Met Lys Val Ser Ala Val Leu Leu Cys Leu Leu Leu Met Thr Ala Ala
 1               5                  10                  15

Phe Asn Pro Gln Gly Leu Ala Gln Pro Asp Ala Leu Asn Val Pro Ser
                20                  25                  30

Thr Cys Cys Phe Thr Phe Ser Ser Lys Lys Ile Ser Leu Gln Arg Leu
            35                  40                  45

Lys Ser Tyr Val Ile Thr Thr Ser Arg Cys Pro Gln Lys Ala Val Ile
 50                  55                  60

Phe Arg Thr Lys Leu Gly Lys Glu Ile Cys Ala Asp Pro Lys Glu Lys
 65                  70                  75                  80

Trp Val Gln Asn Tyr Met Lys His Leu Gly Arg Lys Ala His Thr Leu
                85                  90                  95

Lys Thr

<210> SEQ ID NO 5
<211> LENGTH: 99
<212> TYPE: PRT
<213> ORGANISM: Artificial
<220> FEATURE:
<223> OTHER INFORMATION: Homo sapiens

<400> SEQUENCE: 5

```
Met Lys Val Ser Ala Leu Leu Cys Leu Leu Ile Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                    85                  90                  95

Pro Lys Thr
```

<210> SEQ ID NO 6
<211> LENGTH: 92
<212> TYPE: PRT
<213> ORGANISM: Mus musculus

<400> SEQUENCE: 6

```
Met Lys Val Ser Thr Thr Ala Leu Ala Val Leu Leu Cys Thr Met Thr
1               5                   10                  15

Leu Cys Asn Gln Val Phe Ser Ala Pro Tyr Gly Ala Asp Thr Pro Thr
            20                  25                  30

Ala Cys Cys Phe Ser Tyr Ser Arg Lys Ile Pro Arg Gln Phe Ile Val
        35                  40                  45

Asp Tyr Phe Glu Thr Ser Ser Leu Cys Ser Gln Pro Gly Val Ile Phe
    50                  55                  60

Leu Thr Lys Arg Asn Arg Gln Ile Cys Ala Asp Ser Lys Glu Thr Trp
65                  70                  75                  80

Val Gln Glu Tyr Ile Thr Asp Leu Glu Leu Asn Ala
                85                  90
```

<210> SEQ ID NO 7
<211> LENGTH: 92
<212> TYPE: PRT
<213> ORGANISM: Rattus norvegicus

<400> SEQUENCE: 7

```
Met Lys Leu Cys Val Ser Ala Phe Ser Leu Leu Leu Val Ala Ala
1               5                   10                  15

Phe Cys Asp Ser Val Leu Ser Ala Pro Ile Gly Ser Asp Pro Pro Thr
            20                  25                  30

Ser Cys Cys Phe Ser Tyr Thr Ser Arg Lys Ile His Arg Asn Phe Val
        35                  40                  45

Met Asp Tyr Tyr Glu Thr Ser Ser Leu Cys Ser Gln Pro Ala Val Val
    50                  55                  60

Phe Leu Thr Lys Lys Gly Arg Gln Ile Cys Ala Asp Pro Ser Glu Pro
65                  70                  75                  80

Trp Val Asn Glu Tyr Val Asn Asp Leu Glu Leu Asn
                85                  90
```

<210> SEQ ID NO 8
<211> LENGTH: 100
<212> TYPE: PRT
<213> ORGANISM: Mus musculus

<400> SEQUENCE: 8

```
Met Ala Pro Pro Thr Cys Arg Leu Leu Ser Ala Ala Leu Val Leu Leu
1               5                   10                  15

Leu Leu Leu Ala Thr Asn His Gln Ala Thr Gly Ala Val Val Ala Ser
            20                  25                  30

Glu Leu Arg Cys Gln Cys Leu Lys Thr Leu Pro Arg Val Asp Phe Lys
        35                  40                  45

Asn Ile Gln Ser Leu Ser Val Thr Pro Pro Gly Pro His Cys Ala Gln
    50                  55                  60

Thr Glu Val Ile Ala Thr Leu Lys Gly Gly Gln Lys Val Cys Leu Asp
65                  70                  75                  80

Pro Glu Ala Pro Leu Val Gln Lys Ile Ile Gln Lys Ile Leu Asn Lys
                85                  90                  95

Gly Lys Ala Asn
            100

<210> SEQ ID NO 9
<211> LENGTH: 757
<212> TYPE: DNA
<213> ORGANISM: Homo sapiens

<400> SEQUENCE: 9
ggaaccgaga ggctgagact aacccagaaa catccaattc tcaaactgaa gctcgcactc      60
tcgcctccag catgaaagtc tctgccgccc ttctgtgcct gctgctcata gcagccacct     120
tcattcccca agggctcgct cagccagatg caatcaatgc cccagtcacc tgctgttata     180
acttcaccaa taggaagatc tcagtgcaga ggctcgcgag ctatagaaga atcaccagca     240
gcaagtgtcc caaagaagct gtgatcttca gaccattgt ggccaaggag atctgtgctg      300
accccaagca gaagtgggtt caggattcca tggaccacct ggacaagcaa acccaaactc     360
cgaagacttg aacactcact ccacaaccca agaatctgca gctaacttat tttcccctag     420 cttccccag acaccctgtt ttattttatt ataatgaatt ttgtttgttg atgtgaaaca      480
ttatgcctta agtaatgtta attcttattt aagttattga tgttttaagt ttatctttca     540
tggtactagt gttttttaga tacagagact tggggaaatt gcttttcctc ttgaaccaca     600
gttctacccc tgggatgttt tgagggtctt tgcaagaatc attaatacaa agaatttttt     660
ttaacattcc aatgcattgc taaaatatta ttgtggaaat gaatattttg taactattac     720
accaaataaa tatattttg tacaaaaaaa aaaaaaa                              757

<210> SEQ ID NO 10
<211> LENGTH: 1351
<212> TYPE: DNA
<213> ORGANISM: Homo sapiens

<400> SEQUENCE: 10
gtgatggaga gcaccagcaa agccttaggg cccatccctg gcctcctgtt acccacagag      60
gggtaggccc ttggctctct tccactatga cgtcagcttc cattcttcct ttcttataga     120
caattttcca tttcaaggaa atcagagccc ttaatagttc agtgaggtca ctttgctgag     180
cacaatccca taccctcag cctctgctcc acagagccta agcaaaagat agaaactcac      240
aacttccttg ttttgttatc tggaaattat cccaggatct ggtgcttact cagcatattc     300
aaggaaggtc ttacttcatt cttccttgat tgtgaccatg cccaggctct ctgctcccta     360
taaaaggcag gcagagccac cgaggagcag agaggttgag aacaacccag aaaccttcac     420
ctctcatgct gaagctcaca cccttgccct ccaagatgaa ggtttctgca gcgcttctgt     480
```

```
gcctgctgct catggcagcc actttcagcc ctcagggact tgctcagcca gattcagttt      540
ccattccaat cacctgctgc tttaacgtga tcaataggaa aattcctatc cagaggctgg      600
agagctacac aagaatcacc aacatccaat gtcccaagga agctgtgatc ttcaagacca      660 aacgggcaa ggaggtctgt gctgacccca aggagagatg ggtcagggat tccatgaagc       720
atctggacca atatttcaa atctgaagc catgagcctt catacatgga ctgagagtca        780
gagcttgaag aaaagcttat ttattttccc caacctcccc caggtgcagt gtgacattat      840
tttattataa catccacaaa gagattattt ttaaataatt taaagcataa tatttcttaa      900
aaagtattta attatattta agttgttgat gttttaactc tatctgtcat acatcctagt     960
gaatgtaaaa tgcaaaatcc tggtgatgtg ttttttgttt ttgttttcct gtgagctcaa     1020
ctaagttcac ggcaaaatgt cattgttctc cctcctacct gtctgtagtg ttgtggggtc    1080
ctcccatgga tcatcaaggt gaaacacttt ggtattcttt ggcaatcagt gctcctgtaa    1140
gtcaaatgtg tgctttgtac tgctgttgtt gaaattgatg ttactgtata aactatgga     1200 attttgaaaa aaaatttcaa aagaaaaaa atatatataa tttaaaacta aaaaaaaaa      1260 aaaaaaaaaa aaaaaaaaaa aaaaaaaaaa aaaaaaaaaa aaaaaaaaaa aaaaaaaaaa    1320
aaaaaaaaaa aaaaaaaaaa aaaaaaaaaa a                                   1351

<210> SEQ ID NO 11
<211> LENGTH: 810
<212> TYPE: DNA
<213> ORGANISM: Homo sapiens

<400> SEQUENCE: 11
agcagagggg ctgagaccaa accagaaacc tccaattctc atgtggaagc ccatgccctc       60
accctccaac atgaaagcct ctgcagcact tctgtgtctg ctgctcacag cagctgcttt      120
cagcccccag gggcttgctc agccagttgg gattaatact tcaactacct gctgctacag      180
atttatcaat aagaaaatcc ctaagcagag gctggagagc tacagaagga ccaccagtag      240
ccactgtccc cgggaagctg taatcttcaa gaccaaactg gacaaggaga tctgtgctga      300
ccccacacag aagtgggtcc aggactttat gaagcacctg gacaagaaaa cccaaactcc      360
aaagctttga acattcatga ctgaactaaa aacaagccat gacttgagaa acaaataatt      420
tgtataccct gtcctttctc agagtggttc tgagattatt ttaatctaat tctaaggaat      480
atgagcttta tgtaataatg tgaatcatgg ttttttcttag tagattttaa aagttattaa     540
tattttaatt taatcttcca tggattttgg tgggttttga acataaagcc ttggatgtat      600
atgtcatctc agtgctgtaa aaactgtggg atgctcctcc cttctctacc tcatgggggt      660
attgtataag tccttgcaag aatcagtgca aagatttgct ttaattgtta agatatgatg      720
tccctatgga agcatattgt tattatataa ttacatattt gcatatgtat gactcccaaa      780
ttttcacata aaatagattt ttgtaaaaaa                                       810

<210> SEQ ID NO 12
<211> LENGTH: 861
<212> TYPE: DNA
<213> ORGANISM: Homo sapiens

<400> SEQUENCE: 12
aaaaggccgg cggaacagcc agaggagcag agaggcaaag aaacattgtg aaatctccaa        60
ctcttaacct tcaacatgaa agtctctgca gtgcttctgt gcctgctgct catgacagca      120
gctttcaacc cccagggact tgctcagcca gatgcactca acgtcccatc tacttgctgc     180
```

```
ttcacatttta gcagtaagaa gatctccttg cagaggctga agagctatgt gatcaccacc      240
agcaggtgtc cccagaaggc tgtcatcttc agaaccaaac tgggcaagga gatctgtgct      300
gacccaaagg agaagtgggt ccagaattat atgaaacacc tgggccggaa agctcacacc      360
ctgaagactt gaactctgct acccctactg aaatcaagct ggagtacgtg aaatgactt      420 tccattctcc tctggcctcc tcttctatgc tttggaatac ttctaccata attttcaaat      480
aggatgcatt cggttttgtg attcaaaatg tactatgtgt taagtaatat tggctattat      540
ttgacttgtt gctggtttgg agtttatttg agtattgctg atcttttcta aagcaaggcc      600
ttgagcaagt aggttgctgt ctctaagccc ccttcccttc cactatgagc tgctggcagt      660
gggtttgtat tcggttccca ggggttgaga gcatgcctgt gggagtcatg gacatgaagg      720
gatgctgcaa tgtaggaagg agagctcttt gtgaatgtga ggtgttgcta aatatgttat      780
tgtggaaaga tgaatgcaat agtaggactg ctgacatttt gcagaaaata cattttattt      840
aaaatctcct aaaaaaaaaa a                                                 861

<210> SEQ ID NO 13
<211> LENGTH: 396
<212> TYPE: DNA
<213> ORGANISM: Mus musculus

<400> SEQUENCE: 13
tttcgaagtc tttgacctca acatgaagat ttccacactt ctatgcctcc tgctcatagc       60
taccaccatc agtcctcagg tattggctgg accagatgcg gtgagcaccc cagtcacgtg      120
ctgttataat gttgttaagc agaagattca cgtccggaag ctgaagagct acaggagaat      180
cacaagcagc cagtgtcccc gggaagctgt gatcttcagg accatactgg ataaggagat      240
ctgtgctgac cccaaggaga gtgggttaa gaattccata aaccacttgg ataagacgtc      300
tcgaacgtag catccttgaa ccttcatgtc taggctgaga gttccaaaaa ctcttacgta      360
tttccccctg aagttcccca cgggcagtgt gatatt                                396

<210> SEQ ID NO 14
<211> LENGTH: 755
<212> TYPE: DNA
<213> ORGANISM: Rattus norvegicus

<400> SEQUENCE: 14
agaggcagcg agtaccagtc ccttctctgc tctgctgaca agcgcaccct ctgttacctg       60
ctcagcacca tgaaggtctc caccgctgcc cttgctgttc ttctctgcac catggcgctc      120
tggaacgaag tcttctcagc gccatatgga gctgacaccc cgactgcctg ctgcttctcc      180 tatgacggc aaattccacg aaaattcatt gctgactatt ttgagaccag cagcctttgc      240
tcccagccgg gtgtcatttt cctgaccaag agaaaccggc agatctgcgc tgaccccaaa      300
gagacctggg tccaagaata catcactgag ctggaactaa atgcctgaga ttagaggcag      360
caaggaaccc ccaaacctcc gtgggccccg tgtagagcag gggcttgagc cccagaacat      420
tcctgccacc tgcaaatctc cccctcctat aagctgtttg ctgccaagta gccacatcca      480
gggactcttc acttgaattt ttatttaatt taatcctatt gatttaatac tatttaattt      540
tttaatttat tttattgtca catttgtgtt tgtagctatt tattctgaaa gacctcaggg      600
cacattcctc agccctcccc cccctccca gttgctcaca ctgtgtttgg tgacaattat      660
tctaggtaga cgtgatgaca aagtcatgaa ctgacaaatg tacaatggat gctttgtcta      720
taccagagaa ataataaata tgctctttaa caaga                                 755
```

<210> SEQ ID NO 15
<211> LENGTH: 654
<212> TYPE: DNA
<213> ORGANISM: Mus musculus

<400> SEQUENCE: 15

| | | | | | |
|---|---|---|---|---|---|
| gacagcactc | ggccagcttc | tgaagcttct | gggccctgca | gtcccagctc | tgtgcaaacc | 60 |
| taaccccgag | caacaccatg | aagctctgcg | tgtctgccct | ctctctcctc | ttgctcgtgg | 120 |
| ctgccttctg | tgctccaggg | ttctcagcac | caatgggctc | tgaccctccc | acttcctgct | 180 |
| gtttctctta | cacctcccgg | cagcttcaca | gaagctttgt | gatggattac | tatgagacca | 240 |
| gcagtctttg | ctccaagcca | gctgtggtat | tcctgaccaa | agaggcaga | cagatctgtg | 300 |
| ctaaccccag | tgagccctgg | gtcactgagt | acatgagtga | cttggagttg | aactgagcag | 360 |
| ctccagcgca | gggcaggagg | agccacttca | ggagaggcct | cctcagccct | gatgcttctc | 420 |
| actgagaagc | gtccttgctc | ctcacgttca | gatttcctgc | ccctcttctt | aatttaaatc | 480 |
| tctgtgtaga | ctttgttttg | ttttttggg | ggagtattat | ttctattatt | tatgttttag | 540 |
| ttataggacg | cgtgtctccc | atggagatgg | tccaccattg | ctgaaactct | gctattgtgg | 600 |
| atatgactgt | gaaattgatt | tcatgcattt | tcataataaa | tctttcttta | agat | 654 |

<210> SEQ ID NO 16
<211> LENGTH: 1101
<212> TYPE: DNA
<213> ORGANISM: Mus musculus

<400> SEQUENCE: 16

| | | | | | |
|---|---|---|---|---|---|
| actgcacctc | tgggcctcca | gcaagctccc | tcctgtgctc | aagactccaa | ccactctttg | 60 |
| gtccagagcc | atggcccctc | ccactcgcca | gctcctcaat | gctgtactgg | tcctgctcct | 120 |
| cctgctggcc | accaaccatc | agggtacagg | ggttgttgtg | gccagtgagc | tgcgctgtca | 180 |
| atgcctgacg | accctaccaa | gggttgactt | caagaacatc | cagagcttga | cggtgacccc | 240 |
| tccaggaccc | cactgcgccc | agacagaagt | catagccact | cttaaggatg | gtcatgaagt | 300 |
| ttgtctcaac | cctgaagccc | ccttggttca | gaggatcgtc | caaagatac | tgaacaaagg | 360 |
| caaggctaac | tgacctggaa | aggaagaaca | tgggctcctg | tacctcaacg | ggcagaatca | 420 |
| aagagaaaag | aaacaaactg | cacccaggaa | gcctggatcg | tacctgatgt | gcctcgctgt | 480 |
| ctgagtttat | ctatttattt | atatatgtat | ttatttattt | attttcagtg | cctagatgtt | 540 |
| gttacattta | ctatgatatt | taaagatatg | cattggccag | ctcactgtag | tatcttaaga | 600 |
| ggtcatttta | atatgttgaa | gtttattgta | ataatgttca | atgtgttcag | tcagcattat | 660 |
| tttacttatg | tagttggaag | gtgatgcatt | tttaaatcta | tatttattac | tttctggggg | 720 |
| gggagggggga | gttgggtact | gactacacca | cctccacact | gtgatagaga | ttggggatga | 780 |
| gggggggtggg | ggggcaaaca | gacgcagtca | gagggctttc | aaggcaggac | tgtgcctgtc | 840 |
| cacgtcattt | tctgtaagcc | ccgagaaggg | cgggacgact | gttatttctg | tctccgtgtt | 900 |
| tctacactat | gtgtacaaca | tttctgatgc | tgaatgttca | acaatcgtaa | tgtgaatatc | 960 |
| ccctggacat | tctatgtctt | ctctgtaagg | cacagtgcct | cgtttagcaa | ttgttttgtc | 1020 |
| atgctttctc | atgtcttgaa | gtggggacat | ttatttattc | atgtactttt | acaaataaca | 1080 |
| aaaaaaataa | aaattttac | t | | | | 1101 |